(12) United States Patent
Burns et al.

(10) Patent No.: US 8,030,336 B2
(45) Date of Patent: Oct. 4, 2011

(54) NICOTINAMIDE-BASED KINASE INHIBITORS

(75) Inventors: Christopher John Burns, Seddon (AU); Marcel Robert Kling, Bentleigh (AU)

(73) Assignee: YM Biosciences Australia Pty Ltd, Melbourne, Victoria (AU)

( * ) Notice: Subject to any disclaimer, the term of this patent is extended or adjusted under 35 U.S.C. 154(b) by 1283 days.

(21) Appl. No.: 10/537,719

(22) PCT Filed: Dec. 15, 2003

(86) PCT No.: PCT/AU03/01666
§ 371 (c)(1),
(2), (4) Date: Oct. 11, 2006

(87) PCT Pub. No.: WO2004/054977
PCT Pub. Date: Jul. 1, 2004

(65) Prior Publication Data
US 2007/0060619 A1    Mar. 15, 2007

Related U.S. Application Data

(60) Provisional application No. 60/483,400, filed on Jun. 26, 2003.

(30) Foreign Application Priority Data

Dec. 13, 2002 (AU) ................................. 2002953330
Dec. 17, 2002 (AU) ................................. 2002953385

(51) Int. Cl.
*A61K 31/4418* (2006.01)
*C07D 213/80* (2006.01)
(52) U.S. Cl. ........................................ 514/355; 546/316
(58) Field of Classification Search ................ 546/316; 514/355
See application file for complete search history.

(56) References Cited

U.S. PATENT DOCUMENTS 5,756,524 A * 5/1998 Riordan et al. ................ 514/346
2004/0110802 A1 * 6/2004 Thorarensen et al. ........ 514/355

FOREIGN PATENT DOCUMENTS

| JP | 07-048370 | 2/1995 |
| WO | WO-95/25723 | 9/1995 |
| WO | WO-98/38167 | 9/1998 |
| WO | WO-02/44137 | 6/2002 |
| WO | WO-02/64565 | 8/2002 |

OTHER PUBLICATIONS

Balant et al., "Metabolic Considerations, etc.," in Manfred ed, Burger's Medicinal Chemistry and Drug Discovery, 5th ed. vol. 1: Principles and Practice, John Wiley & Sons, Inc., 1995.*
Vippagunta et al., "Crystalline Solids", Advanced Drug Delivery Reviews 48 (2001) 3-26.*
Jain et al., "Polymorphism in Pharmacy", Indian Drugs, 1986, 23(6), 315-329.*
Guillory (in Brittain ed.), "Polymorphism, etc.," NY: Marcel Dekker, Inc., 1999, 1-2, 183-226.*
Supplementary European Search Report for EP 03767297.9, issued Sep. 18, 2007, 1 page.
Traxler, Expert Opinion on Therapeutic Patents (1998) 8(12):1599-1625.
Traxler, Expert Opinion on Therapeutic Patents (1997) 7(6):571-588.
International Search Report for PCT/AU03/001666, mailed on Feb. 18, 2004, 3 pages.
Johnson et al., J. Pharm. Sci. (1973) 62(11):1881-1883.

* cited by examiner

*Primary Examiner* — Patricia Morris
(74) *Attorney, Agent, or Firm* — Morrison & Foerster LLP

(57) ABSTRACT

A compound of the general formula (I) or pharmaceutically acceptable prodrugs, salts, hydrates, solvates, crystal forms or diastereomers thereof is described. A method of treating tyrosine kinase-associated disease states in a subject using a compound of formula (I) is also described.

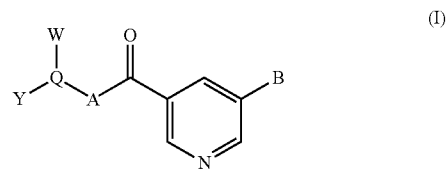

6 Claims, No Drawings

```
                        SEQUENCE LISTING

<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ccgctcgaga ctgaagtgga ccccacacat                                    30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
cggggtacct tattttaaaa gtgcttcaaa                                    30

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
acgcgtcgac ggtgcctttg aagaccggga t                                  31

<210> SEQ ID NO 4
<211> LENGTH: 34
<212> TYPE: DNA
<213> ORGANISM: Artificial Sequence
<220> FEATURE:
<223> OTHER INFORMATION: Primer
```

```
<400> SEQUENCE: 4
atagtttagc ggccgctcag aatgaaggtc attt                              34

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
ccgctcgagt atgcctgcca agaccccacg                                   30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cggggtaccc tatgaaaagg acagggagtg                                   30

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
ggagcactcg agatggtagc acacaaccag gtg                               33

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
ggagcaggaa ttccggcgct gccggtcaaa tctgg                             35

<210> SEQ ID NO 9
<211> LENGTH: 17
<212> TYPE: PRT
<213> ORGANISM: Artificial Sequence
<220> FEATURE:
<223> OTHER INFORMATION: Synthetically engineered gastrin producing
      peptide

<400> SEQUENCE: 9

Glu Gly Pro Trp Leu Glu Glu Glu Glu Ala Tyr Gly Trp Met Asp
 1               5                  10                  15

Phe
```

NICOTINAMIDE-BASED KINASE INHIBITORS

CROSS-REFERENCE TO RELATED APPLICATIONS

This application is the national phase of PCT application PCT/AU2003/001666 having an international filing date of 15 Dec. 2003, which claims priority from Australian applications 200295330, filed 13 Dec. 2002, 2002953385, filed 17 Dec. 2002, and U.S. provisional application 60/483,400, filed 26 Jun. 2003. The contents of these documents are incorporated herein by reference.

FIELD OF THE INVENTION

The present invention involves compounds represented by Formula (I) herein below, pharmaceutical compositions comprising such compounds and methods of suppressing the growth of cancers and other proliferative diseases.

BACKGROUND OF THE INVENTION

Normal cellular proliferation is a well-controlled balance between the rate of cell cycle progression and programmed cell death (apoptosis). This balance is maintained by the appropriate transmission of extracellular signals by intracellular signal transduction circuitry. In tumours this equilibrium becomes disturbed by either unrestrained completion of the cell cycle, or loss of normal apoptotic cell death. In many cases this deregulation comes about by the autonomous activation of the intracellular signal transduction circuitry that controls the cell cycle and apoptosis pathways. Central to the regulation of these pathways are members of the protein kinase family, and a promising avenue to the generation of treatments for hyperproliferative diseases such as cancer, are compounds that target those kinases involved in this regulation.

Protein kinases are a family of enzymes that catalyse the phosphorylation of specific residues in proteins. In general protein kinases fall into several groups; those which preferentially phosphorylate serine and/or threonine residues, those which preferentially phosphorylate tyrosine residues and those which phosphorylate both tyrosine and Ser/Thr residues. Protein kinases are therefore key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis.

Inappropriately high protein kinase activity has been implicated in many diseases resulting from abnormal cellular function. This might arise either directly or indirectly, for example by failure of the proper control mechanisms for a kinase, related for example to mutation, over-expression or inappropriate activation of the enzyme; or by over- or underproduction of cytokines or growth factors also participating in the transduction of signals upstream or downstream of the kinase. In all of these instances, selective inhibition of the action of the kinase might be expected to have a beneficial effect. Diseases where aberrant kinase activity has been implicated include: diabetes; restenosis; atherosclerosis; fibrosis of the liver and kidney; ocular diseases; myelo- and lymphoproliferative disorders; cancer such as prostate cancer, colon cancer, breast cancer, head and neck cancer, leukemia and lymphoma; and, auto-immune diseases such as Atopic Dermatitis, Asthma, rheumatoid arthritis, Crohn's disease, psoriasis, Crouzon syndrome, achondroplasia, and thanatophoric dysplasia.

Protein kinases include, for example, but are not limited to, members of the Protein Tyrosine Kinase family (PTKs), which in turn can be divided into the cytoplasmic PTKs (CTKs) and the receptor PTKs (RTKs). The cytoplasmic PTKS include the SRC family, (including: BLK; FGR; FYN; HCK; LCK; LYN; SRC; YES and YRK); the BRK Family (including: BRK; FRK, SAD; and SRM); the CSK family (including: CSK and CTK); the BTK family, (including BTK; ITK; TEC; MKK2 and TXK), the Janus kinase family, (including: JAKE1, JAK2, JAK3 and Tyk2), the FAK family (including, FAK and PYK2); the Fes family (including FES and FER), the ZAP70 family (including ZAP70 and SYK); the ACK family (including ACK1 and ACK2); and the Abl family (including ABL and ARG). The RTK family includes the EGF-Receptor family (including, EGFR, HER2, HER3 and HER4); the Insulin Receptor family (including INS-R and IGF1-R); the PDGF-Receptor family (including PDGFRα, PDGFRβ, CSP1R, KIT, FLK2); the VEGF-Receptor family (including; FLT1, FLK1 and FLT4); the FGF-Receptor family (including FGFR1, FGFR2, FGFR3 and FCFR4); the CCK4 family (including CCK4); the MET family (including MET and RON); the TRK family (including TRKA, TRKB, and TRKC); the AXL family (including AXL, MER, and SKY); the TIE/TEK family (including TIE and TIE2/TEK); the EPH family (including EPHA1, EPHA2, EPHA3, EPHA4, EPHA5, EPHA6, EPHA7, EPHA8, EPHB1, EPHB2, EPHB3, EPHB4, EPHB5, EPHB6); the RYK family (including RYK); the MCK family (including MCK and TYRO10); the ROS family (including ROS); the RET family (including RET); the LTK family (including LTK and ALK); the ROR family (including ROR1 and ROR2); The Musk family (including Musk); the LMR family including LMR1, LMR2 and LMR3); and the SuRTK106 family (including SuRTK106).

Similarly, the saline/threonine specific kinases (STKs) comprise a number of distinct sub-families, including; the extracellular signal regulated kinases, (p42/ERK2 and p44/ERK1); c-Jun NH2-terminal kinase (JNK); cAMP-responsive element-binding protein kinases (CREBK); cAMP-dependent kinase (CAPK); mitogen-activated protein kinase-activated protein kinase (MAPK and its relatives); stress-activated protein kinase p38/SAPK2; mitogen-and stress-activated kinase (MSK); protein kinases, PKA, PKB and PKC inter alia. Additionally, the genomes of a number of pathogenic organisms possess genes encoding protein kinases. For example, the malarial parasite Plasmodium falciparum and viruses such as HPV and Hepatitis viruses appear to bear kinase related genes.

In one embodiment, the method of the invention is used in the treatment of sarcomas, carcinomas and/or leukemias. Exemplary disorders for which the subject method can be used alone or as part of a treatment regimen include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma; Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the method of the invention is be used to treat disorders such as carcinomas forming from tissue of the breast, prostate, kidney, bladder or colon.

In other embodiments, the method of the invention is used to treat hyperplastic or neoplastic disorders arising in adipose tissue, such as adipose cell tumors, e.g., lipomas, fibrolipomas, lipoblastomas, lipomatosis, hibernomas, hemangiomas and/or liposarcomas.

SUMMARY OF THE INVENTION

The present inventors have found that a group of compounds based upon a disubstituted pyridine scaffold are inhibitors of the growth and proliferation of cancer cells.

Accordingly, in a first aspect the present invention provides a compound of the general formula

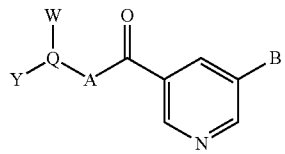

I or pharmaceutically acceptable prodrugs, salts, hydrates, solvates, crystal forms or diastereomers thereof, wherein:
A is selected from O, S, NR1, where R1 is selected from H, $C_{1-4}$ alkyl;
B is aryl, hetaryl optionally substituted with 0-3 substituents independently chosen from halogen, $C_{1-4}$alkyl, $CF_3$, CN, aryl, hetaryl, OH, $OCF_3$, $OC_{1-4}$alkyl, $OC_{2-5}$alkylNR2R3, Oaryl, Ohetaryl, $CO_2R2$, CONR2R3, NR2R3, $C_{1-4}$ alkylNR2R3, $NR4C_{1-4}$alkylNR2R3, NR2COR3, OC(O)NR2R3, NR4CONR2R3, $NR2SO_2R3$; and R2, R3 are each independently H, $C_{1-4}$ alkyl, $C_{1-4}$ alkyl heterocyclyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR5; and R4 is selected from H, $C_{1-4}$ alkyl; and R5 is selected from H, $C_{1-4}$ alkyl;
Q is a bond, or $C_{1-4}$ alkyl;
W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, $NR_6C(O)R7$, CONR6R7, OR6, NR6R7; and R6, and R7 are each independently H, $C_{1-4}$ alkyl, $C_{1-4}$ alkyl cycloalkyl, $C_{1-4}$ alkyl heterocyclyl, aryl, hetaryl, or may be joined to form an optionally substituted 3-8 membered ring optionally containing an atom selected from O, S, NR8 and R8 is selected from H, $C_{1-4}$ alkyl;
Y is H, aryl or hetaryl optionally substituted with 0-3 substituents independently chosen from halogen, $C_{1-4}$ alkyl, $CF_3$, aryl, hetaryl, OH, $OCF_3$, CN, $C_{2-4}$alkynyl, $OC_{1-4}$ alkyl, $OC_{2-5}$alkylNR9R10, Oaryl, Ohetaryl, $CO_2R9$, CONR9R10, NR9R10, $C_{1-4}$ alkylNR9R10, $NR11C_{1-4}$alkylNR9H10, NR9COR10, NR11CONR9R10, $NR9SO_2R10$; and R9, R10 are each independently H, $C_{1-4}$ alkyl, $C_{1-4}$ alkyl heterocyclyl, aryl, hetaryl, $C_{1-4}$ alkyl aryl, $C_{1-4}$ alkyl hetaryl, or may be joined to form an optionally substituted 3-8 membered ring optionally containing an atom selected front O, S, NR12; and R11 is selected from H, $C_{1-4}$ alkyl; and R12 is selected from H, $C_{1-4}$ alkyl.

In a second aspect the present invention provides a composition comprising a carrier and at least one compound of the first aspect of the invention.

In a third aspect the present invention provides a method of treating a tyrosine kinase-associated disease state in a subject, the method comprising administering a therapeutically effective amount of at least one compound of the first aspect of the invention or a therapeutically effective amount of a composition of the second aspect of the invention.

DETAILED DESCRIPTION OF THE INVENTION

In a first aspect the present invention provides a compound of the general formula

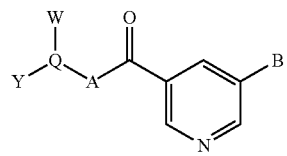

I or pharmaceutically acceptable prodrugs, salts, hydrates, solvates, crystal forms or diastereomers thereof, wherein:
A is selected from O, S, NR1, where R1 is selected from H, $C_{1-4}$ alkyl;
B is aryl; hetaryl optionally substituted with 0-3 substituents independently chosen from halogen, $C_{1-4}$ alkyl, $CP_3$, CN, aryl, hetaryl, OH, $OCF_3$, $OC_{1-4}$alkyl, $OC_{2-5}$alkylNR2R3, Oaryl, Ohetaryl, $CO_2R2$, CONR2R3, NR2R3, $C_{1-4}$alkylNR2R3, $NR4C_{1-4}$alkylNR2R3, NR2COR3, OC(O)NR2R3, NR4CONR2R3, $NR2SO_2R3$; and R2, R3 are each independently H, $C_{1-4}$ alkyl, $C_{1-4}$ alkyl heterocyclyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR5; and R4 is selected from H, $C_{1-4}$ alkyl; and R5 is selected from H, $C_{1-4}$ alkyl;
Q is a bond, or $C_{1-4}$ alkyl;
W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, $NR_6C(O)R7$, CONR6R7, OR6, NR6R7; and R6, and R7 are each independently H, $C_{1-4}$ alkyl, $C_{1-4}$ alkyl cycloalkyl, $C_{1-4}$ alkyl heterocyclyl, aryl, hetaryl, or may be joined to form an optionally substituted 3-8 membered ring optionally containing an atom selected from O, S, NR8 and R8 is selected from H, $C_{1-4}$ alkyl;
Y is H, aryl or hetaryl optionally substituted with 0-3 substituents independently chosen from halogen, $C_{1-4}$alkyl, $CF_3$, aryl, hetaryl, OH, $OCF_3$, CN, $C_{2-4}$ alkynyl, $OC_{1-4}$ alkyl, $OC_{2-5}$alkylNR9R10, Oaryl, Ohetaryl, $CO_2R9$, CONR9R10, NR9R10, $C_{1-4}$ alkylNR9R$_{10}$, $NR11C_{1-4}$alkylNR9R10, NR9COR10, NR11CONR9R10, $NR9SO_2R10$; and R9, R10 are each independently H, $C_{1-4}$ alkyl, $C_{1-4}$ alkyl heterocyclyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR12; and R11 is selected from H, $C_{1-4}$ alkyl; and R12 is selected from H, $C_{1-4}$ alkyl.

In the above description it will be appreciated that:

$C_{1-4}$ alkyl means an unsubstituted or optionally substituted straight or branched alkyl chain Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3-8 membered saturated ring

Heterocyclyl means a 3-8 membered saturated ring containing 1-3 heteroatoms selected from O, S, NR13, where R13 is H, $C_{1-4}$ alkyl, aryl, hetaryl.

Preferably, the compound is selected from the compounds of Table 1 and Table 2.

In a further preferred embodiment the compound is selected from compounds of the general formula II.

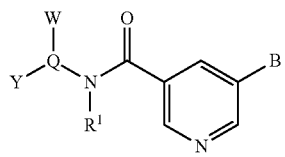

II or pharmaceutically acceptable prodrugs, salts, hydrates, solvates, crystal forms or diastereomers thereof, wherein:

R1 is selected from H, $C_{1-4}$ alkyl;

B is aryl, hetaryl optionally substituted with 0-3 substituents independently chosen from halogen, $C_{1-4}$ alkyl, $CF_3$, aryl, hetaryl, OH, $OCF_5$, $OC_{1-4}$alkyl, $OC_{2-5}$alkylNR2R3, Oaryl, Ohetaryl, $CO_2R2$, CONR2R3, NR2R3, $C_{1-4}$alkylNR2R3, $NR4C_{1-4}$alkylNR2R3, NR2COR3, NR4CONR2R3, $NR2SO_2R3$; and R2, R3 are each independently H, $C_{1-4}$ alkyl, $C_{1-4}$ alkyl heterocyclyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR5; and R4 is selected from H, $C_{1-4}$ alkyl; and R5 is selected from H, $C_{1-4}$ alkyl;

Q is a bond, or $C_{3-4}$ alkyl;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR6R7; and R6, and R7 are each independently H, alkyl, $C_{1-4}$ alkyl cycloalkyl, $C_{1-4}$ alkyl heterocyclyl, aryl, hetaryl, or may be joined to form an optionally substituted 3-8 membered ring optionally containing an atom selected from O, S, NR8 and R8 is selected from H, $C_{1-4}$ alkyl;

Y is H, aryl or hetaryl optionally substituted with 0-3 substituents independently chosen from halogen, $C_{1-4}$ alkyl, $CF_3$, aryl, hetaryl, OH, $OCF_3$, $OC_{1-4}$alkyl, $OC_{2-5}$alkylNR9R10, Oaryl, Ohetaryl, $CO_2R9$, CONR9R10, NR9R10, $C_{1-4}$ alkylNR9R10, $NR11C_{1-4}$alkylNR9R10, NR9COR10, NR11CONR9R10, $NR9SO_2R10$; and R9, R10 are each independently H, $C_{1-4}$ alkyl, $C_{1-4}$ alkyl heterocyclyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR12; and R11 is selected from H, $C_{1-4}$ alkyl; and R12 is selected from H, $C_{1-4}$ alkyl.

In the above description it will be appreciated that $C_{1-4}$ alkyl means an unsubstituted or optionally substituted straight or branched alkyl chain Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3-8 membered saturated ring

Heterocyclyl means a 3-8 membered saturated ring containing 1-3 heteroatoms selected from O, S, NR13, where R13 is H, $C_{1-4}$ alkyl, aryl, hetaryl.

The compounds of this invention include all conformational isomers (eg. cis and trans isomers). The compounds of the present invention may have asymmetric centers and therefore may exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula I may also exist as tautomers. This invention relates to the use of all such tautomers and mixtures thereof.

This invention also encompasses pharmaceutical compositions containing prodrugs of compounds of the formula I. This invention also encompasses methods of treating or preventing disorders that can be treated or prevented by the inhibition of protein kinases comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvaline, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I. Prodrugs also include compounds wherein acyloxyalkyl or phosphonooxyalkyl moieties are covalently attached to compounds of formula I possessing a free hydroxyl group. Acyloxyalkyl or phosphonooxyalkyl moieties may also be covalently attached to compounds of formula I possessing a pyridyl ring through formation of a N-(acyloxyalkyl)- or N-(phosphonooxyalkyl)-pyridinium salt. This invention also encompasses pharmaceutical compositions containing prodrugs of compounds of the formula I.

In a second aspect the present invention provides a composition comprising a carrier and at least one compound of the first aspect of the invention.

In a third aspect the present invention provides a method of treating a tyrosine kinase-associated disease state, the method comprising administering a therapeutically effective amount of at least one compound of the first aspect of the invention or a therapeutically effective amount of a composition of the second aspect of the invention.

In a preferred embodiment of the present invention the disease state is selected from the group consisting of Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; Rheumatic Diseases, such as Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis; Other autoimmune diseases such as Type I diabetes, autoimmune thyroid disorders, and Alzheimer's disease; Viral Diseases, such as Epstein Barr Virus (EBV), Hepatitis B, Hepatitis C, HIV, HTLV1, Varicella-Zoster Virus (VZV), Human Papilloma Virus (HPV); Cancer, such as fibrosarcoma, myxosarcoma, liposarcoma, chondrosarcoma, osteogenic sarcoma, chordoma, angiosarcoma, endothellosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, and carcinomas forming from tissue of the breast, prostate, kidney, bladder or colon, and neoplastic disorders arising in adipose tissue, such as adipose cell tumors, e.g., lipomas, fibrolipomas, lipoblastomas, lipomatosis, hibemomas, hemangiomas and/or liposarcomas.

As used herein the term "tyrosine kinase-associated disease state" refers to those disorders which result from aberrant tyrosine kinase activity and/or which are alleviated by inhibition of one or more of these enzymes.

The present invention provides pharmaceutical compositions comprising at least one of the compounds of the formula I or II capable of treating a kinase associated disorder in an amount effective therefore, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation.

The compounds of the formula I or II may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which cell growth inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen, aspirin, acetaminophen and cyclooxygenase inhibitors such as rofecoxib, steroids such as prednisolone or dexamethasone, gold compounds, antiproliferative agents such as methotrexate, FK506 (tacrolimus, Prograf), mycophenolate mofetil, antineoplastic agents such as azathioprine, VP-16, etoposide, fludarabine, cisplatin, doxorubicin, adriamycin, amsacrine, camptothecin, cytarabine, gemcitabine, vinblastine, vincristine, fluorodeoxyuridine, melphalan and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

The pharmaceutical composition and method of the present invention may further comprise other therapeutically active compounds as noted herein which are known inhibitors or substrates of drug efflux systems or drug detoxification and excretory systems. Such systems include P-glycoprotein, multidrug resistance-associated protein, lung resistance protein and glutathione S-transferase isoenzymes alpha, mu, pi, sigma, theta, zeta and kappa. Co-administration of drugs known to inhibit or reduce the activity of these systems may increase the efficacy of the compounds described in the present invention through increasing the amount of therapeutic agent in the cell. Using this approach, one may be able to achieve therapeutic efficacy with lower dosages, thus reducing the potential for adverse side effects. Examples of inhibitors or substrates for these systems include; verapamil, probenecid, dipyridamole, ethacrynic acid, indomethacin, sulfasalazine, buthionine sulfoximine, cyclosporin A and tamoxifen.

In the treatment or prevention of conditions which require protein tyrosine kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Throughout this specification the word "comprise", or variations such as "comprises" or "comprising", will be understood to imply the inclusion of a stated element; integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more dearly understood preferred forms thereof will now be described by reference to the following non-limiting Examples.

EXAMPLES

MATERIALS AND METHODS:

Compound Synthesis

Compounds arc generally prepared in a 2-step process starting from a protected 5-bromonicotinic acid.

The first step of the synthesis typically involves a palladium mediated cross-coupling of the protected 5-bromonicotinic acid with a suitably functionalised coupling partner. Typical coupling partners are boronic acids (Suzuki coupling: see for example Miyaura, N. and Suzuki, *Chem Rev.* 1995, 952457) or organostannanes (Stille coupling: see for example Stille, J. K., *Angew. Chem., Int. Ed. Engl.,* 1986, 25, 508) (Scheme 1).

Scheme I

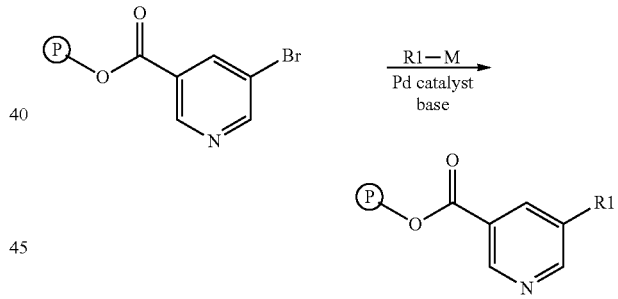

The Suzuki coupling is the preferred coupling method and is typically performed in a solvent such as DME, THP, DMF, ethanol, propanol, toluene, or 1,4-dioxane in the presence of a base such as potassium carbonate, sodium carbonate, lithium hydroxide, caesium carbonate, sodium hydroxide, potassium fluoride or potassium phosphate. The reaction may be carried out at elevated temperatures and the palladium catalyst employed may be selected from Pd(PPh$_3$)$_4$, Pd(OAc)$_2$, [PdCl$_2$(dppf)], Pd$_2$(dba)$_3$/P(t-Bu)$_3$, palladium on carbon.

Methods to protect 5-bromonicotinic acid are known to those skilled in the art and may include the formation of a 2-(trimethylsilyl)ethyl ester, 2-(trimethylsilyl)ethoxymethyl ester, tetrahydrofuranyl ester or t-butyl ester. The t-butyl ester is the preferred protecting group.

The t-Butyl 5-bromonicotinate employed in the first step can be readily prepared from commercial 5-bromonicotinic acid using conventional methods well known to those skilled in the art. These methods include the coupling of 5-bromonicotinic acid with t-butanol using coupling reagents such as dicyclohexylcarbodiimide or 1-(3-dimethylaminopropyl)-3-ethylcarbodiimide in a solvent such as dichloromethane, or treatment of 5-bromonicotinic acid with di-t-butyldicarbonate in the presence of a base such as triethylamine in a solvent such as tetrahydrofuran.

The second step of the synthesis is amide, ester or thioester formation by coupling the 5-arylnicotinic acid with a primary or secondary amine, an alcohol or phenol, or an alkyl or aryl mercaptan (Scheme 2).

Scheme 2

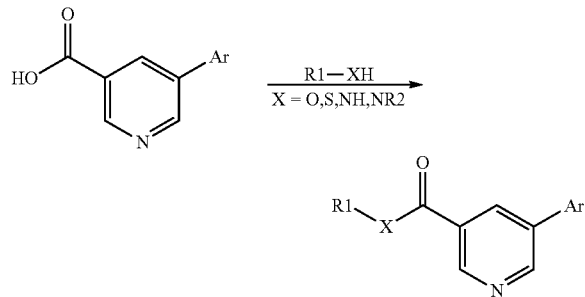

Initially the protected ester forms of the 5-arylnicotinate derivatives prepared as in Scheme 1 are cleaved to the corresponding acids using methods well known to those skilled in the art.

The 5-arylnicotinic acid derivatives are typically coupled with amines, alcohols, phenols, thiols or thiophenols using coupling reagents such as dicyclohexylcarbodiimide, 1-(3-dimethylaminopropyl)-3-ethylcarbodiimide, diisopropylcarbodiimide or carbonyldiimidazole in solvents such as dichloromethane and tetrahydrofuran.

Alternatively, the deprotected 5-arylnicotinic acid derivatives prepared as in Scheme 1 can be converted to the respective acid chloride derivatives using thionyl chloride or oxalyl chloride, or to the mixed anhydride species using, for example, t-butyl chloroformate, using procedures well known to those skilled in the art. The acid chloride or mixed anhydride derivatives can then be reacted with the desired amine, alcohol phenol, thiol or thiophenol in the presence of a base such as triethylamine, diisopropylethylamine or solid phase equivalent in a solvent such as dichloromethane, tetrahydrofuran, dioxane or ethyl acetate at ambient or elevated temperatures, to generate the desired 5-aryl nicotinic acid derivatives.

As a further alternative, the deprotected 5-arylnicotinic acid derivatives prepared as in Scheme 1 can be converted to the corresponding active ester intermediates, such as the succinimidyl, pentafluorophenyl or p-nitrophenyl esters. This can be achieved by coupling the 5-arylnicotinic acid derivatives with N-hydroxysuccinimide, pentafluorophenol or p-nitrophenol using coupling reagents such as dicyclohexylcarbodiimide, 1-(3-dimethylaminopropyl)-3-ethylcarbodiimide, diisopropylcarbodiimide or carbonyldiimidazole in solvents such as dichloromethane and tetrahydrofuran. Active acyl intermediates can also be formed directly by reaction of the 5-arylnicotinic acid derivatives with reagents such as diphenylphosphoryl azide, pentafluorophenyl acetate, pentafluorophenyl diphenylphosphinate or cyanuric chloride using methods well known to those skilled in the art.

The products formed from this reaction sequence may be further derivatised using techniques well known to those skilled in the art.

Example 1

Tert-Butyl 5-bromonicotinate

To a mixture of 5-bromonicotinic acid (0.30 g, 1.49 mmol) and di-tert-butyldicarbonate (0.45 g, 2.06 mmol) in THF (15 mL) was added triethylamine (0.25 mL, 1.79 mmol) followed by 4-(pyrrolidino)pyridine (30 mg, 0.20 mmol). The resultant solution was stirred at ambient temperature for 48 hr. The volatiles were then removed under vacuum and the residue was purified by column chromatography on silica (gradient, $CH_2Cl_2$ to 3% $MeOH/CH_2Cl_2$) to provide the product as a white solid (0.35 g, 91%)

$^1$H-n.m.r. ($CDCl_3$) δ1.60 (s, 9H, t-butyl), 8.35 (m, 1H, Ar), 8.79 (d, J2.5 Hz, 1H, Ar), 9.06 (d, J 1.4 Hz, 1H, Ar).

Example 2

Tert-Butyl 5-(3,4-methylenedioxyphenyl)nicotinate

In a flask was placed tert-butyl 5-bromonicotinate (1.00 g, 3.87 mmol), 10% w/w palladium on carbon (210 mg, ~0.2 mmol Pd), potassium carbonate (1.10 g, 7.96 mmol), 3,4-methylenedioxy-phenyl boronic acid (0.96 g, 5.79 mmol), dimethylformamide (50 mL) and water (250 L). The flask was purged with nitrogen and then heated, with stirring, to 90° C. for 15 hr. The reaction mixture was allowed to cool, diluted with water (350 mL) and extracted with $CH_2Cl_2$ (4X). The combined extracts was washed with water, dried ($MgSO_4$) and concentrated in vacuo. The crude residue was purified by flash chromatography on silica (gradient, $CH_2Cl_2$ to 50% ether/$CH_2Cl_2$) to provide an off-white solid (1.02 g, 88%).

$^1$H-n.m.r. ($CDCl_3$) δ1.63 (s, 9H, t-butyl), 6.04 (s, 2H, $CH_2$), 6.90 (m, 1H, Ar), 7.08 (m, 2H, Ar), 8.34 (m, 1H, Ar), 8.89 (d, J1.9 Hz, 1H, Ar), 9.09 (d, J2.0 Hz, 1H, Ar).

Example 3

5-(3,4-methylenedioxyphenyl)nicotinoyl chloride

A solution of tert-butyl 5-(3,4-methylenedioxyphenyl) nicotinate (0.80 g, 2.67 mmol) in trifluoroacetic acid (10 mL) was stirred at room temperature for 2 hr. The trifluoroacetic acid was removed in vacuo and the residue treated twice with toluene followed by removal under vacuum (to remove residual TFA). The yellow/green residue was then treated with thionyl chloride (10 mL) and dimethylformamide (100 L) and the mixture was heated to reflux for 15 hr. The reaction mixture was allowed to cool to ambient temperature, then the Volatiles were removed on a water aspirator. The residue was treated twice with toluene followed by removal in vacuo to leave a yellow solid. To the crude acid chloride was added 1,4-dioxane (16 mL) to make a 0.167 M suspension, which was used without further treatment in the next step.

Example 4

Formation of Nicotinamides in 96-well Format.

To each well of a 96-well deep well plate was added Amberlyst A-21 resin (70 mg, 0.33 mmol). To each well was then added a 0.19 M 1,4-dioxane solution of amine (0.30 mL, 57 mol) followed by a 0.167 M suspension of 5-arylnicotinoyl chloride (0.48 mL, 80 mol). The plate was sealed with a webseal mat and the plate was sonicated for 1 hr in a sonicator bath. Amberlite IRA-67 (30 mg, 0.17 mmol) was added to each well, the plate was re-sealed and sonication continued for a further 30 min. The contents of the 96-well plate was transferred via pipettor to a 96-well filter plate and filtered into a second 96-well deep well plate. 1,4-Dioxane (0.40 mL) was placed in each well of the original 96-well plate (to rinse). This was aspirated with the pipettor and then transferred to the filter plate and filtered into the second 96-well plate. The second 96-well plate was stripped of all volatiles on a Christ rotary vacuum concentrator, and then the residues in each well were re-dissolved in $CH_2Cl_2$ (0.50 mL). These $CH_2Cl_2$ solutions were transferred to a second filter plate loaded with silica (200 mg/well) and filtered into a third 96-well deep well plate. A 10% methanol/$CH_2Cl_2$ solution (0.50 mL) was added to each well of the second filter plate and filtered into the third deep well plate. The contents of the third plate was analysed by LC-MS and then concentrated under vacuum using the Christ rotary vacuum concentrator.

Further examples of 5-arylnicotinamides are shown in Table 1 along with their experimental m/z values.

TABLE 1

| CHEMISTRY | m/z (EI) |
|---|---|
| C22H22N2O2 | 346.6 |
| C20H19N3O2 | 333.6 |
| C17H20N2O2 | 284.4 |
| C22H22N2O2 | 346.6 |
| C18H20N2O4 | 327.8 |

TABLE 1-continued
| CHEMISTRY | m/z (EI) |
|---|---|
| <br>C20H15FN2O3 | 351.2 |
| 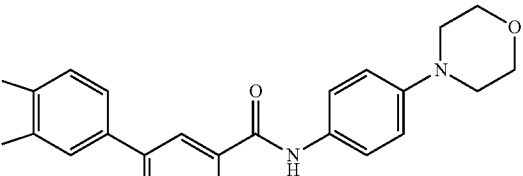<br>C23H21N3O4 | 404.2 |
| 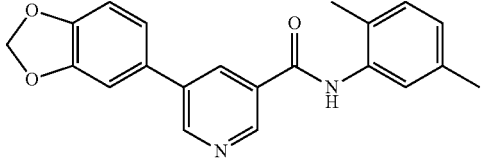<br>C21H18N2O3 | 347.1 |
| 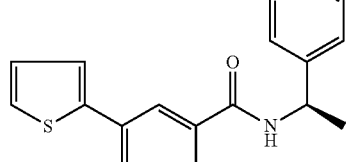<br>C18H16N2OS | 309.9 |
| 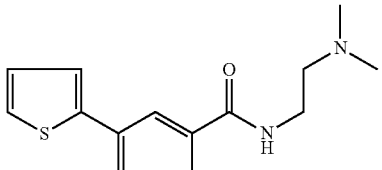<br>C14H17N3OS | 274.3 |
| 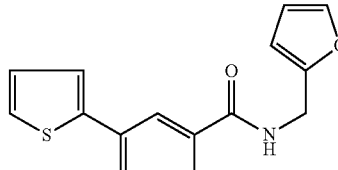<br>C15H12N2O2S | 286.1 |

TABLE 1-continued
| CHEMISTRY | m/z (EI) |
|---|---|
| 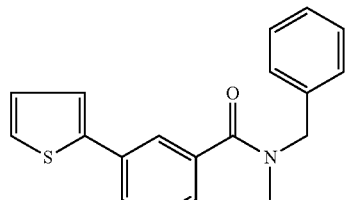<br>C18H16N2OS | 310.1 |
| 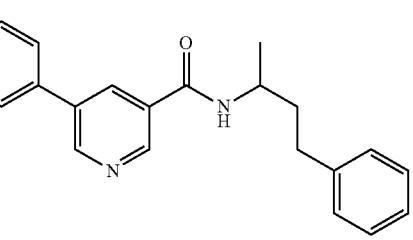<br>C21H21N3O | 331.2 |
| 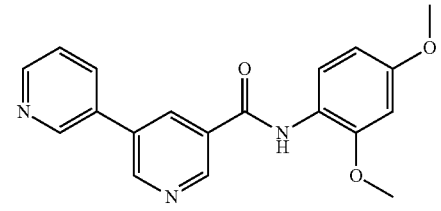<br>C19H17N3O3 | 335.4 |
| 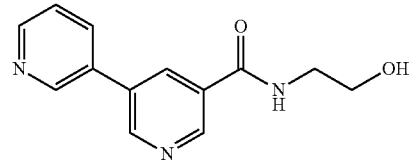<br>C13H13N3O2 | 225.2<br>(M-18) |
| 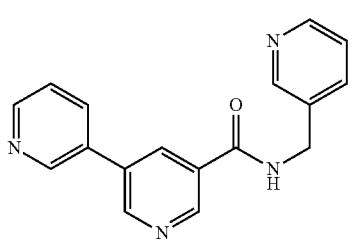<br>C17H14N4O | 290.0 |
| 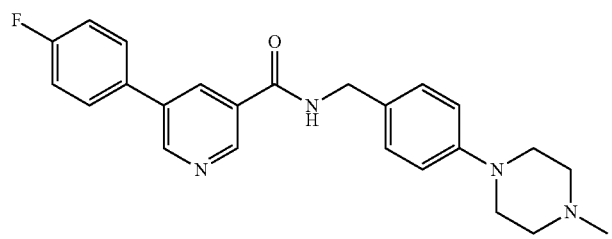<br>C24H25FN4O | 405.4 |

TABLE 1-continued
| CHEMISTRY | m/z (EI) |
|---|---|
| 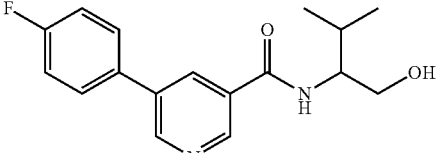<br>C17H19FN2O2 | 302.0 |
| 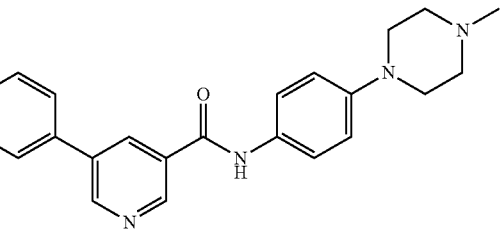<br>C23H23FN4O | 391.4 |
| 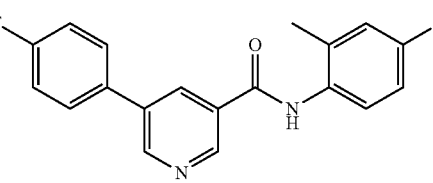<br>C19H14F2N2O | 325.2 |
| 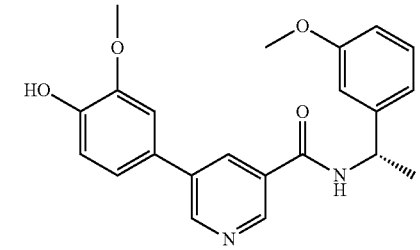<br>C22H22N2O4 | 378.4 |
| 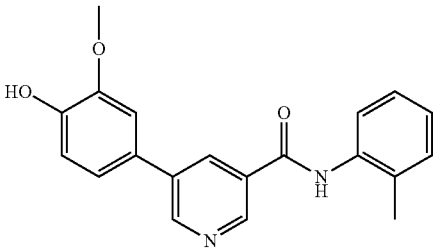<br>C20H18N2O3 | 334.2 |
| 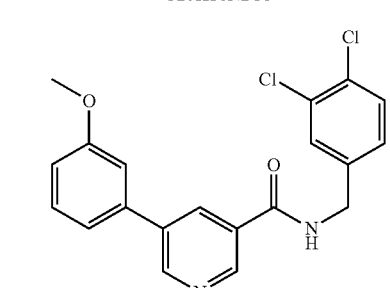<br>C20H16Cl2N2O2 | 385.3 |

TABLE 1-continued

| CHEMISTRY | m/z (EI) |
|---|---|
| 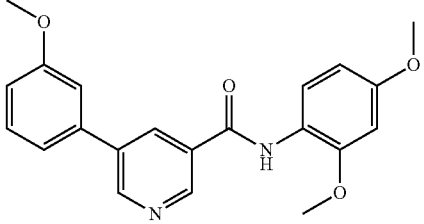 C21H20N2O4 | 366.0 |

SCREENING

JAK Tyrosine Kinase Domain Production

JAK kinase domains were produced in the following manner:

JAK1.

The kinase domain of human JAK1 was amplified from U937mRNA using the polymerase chain reaction with the following primers:

```
                                    (SEQ ID NO: 1)
XHOI-J1   5'-CCG CTC GAG ACT GAA GTG GAC CCC ACA
          CAT-3'
                                    (SEQ ID NO: 2)
J1-KPNI   5'-CGG GGT ACC TTA TTT TAA AAG TGC TTC
          AAA-3'
```

JAK1 PCR products were cloned into the pFastBac HTb expression vector (Gibco) via the Xho I and Kpn I Sites. The JAK1 plasmid was then transformed into competent DH10Bac cells (Gibco), and the recombinant baculovirus produced prepared for transfection into Sf9 insect cells.

JAK2

The kinase domain of human JAK2 was amplified from U937mRNA using the polymerase chain reaction with the following primers:

```
                                    (SEQ ID NO: 3)
SALI-jk2  5'-ACG CGT CGA CGG TGC CTT TGA AGA CCG
          GGA T-3'
                                    (SEQ ID NO: 4)
jk2-NOTI  5'-ATA GTT TAG CGG CCG CTC AGA ATG AAG
          GTC ATT T-3'
```

JAK2 PCR products were doped into the pFastBac HTc expression vector (Gibco) via the Sal I and Not I sites. The JAK2 plasmid was than transformed into competent DH10Bac cells (Gibco), and the recombinant baculovirus produced prepared for transfection into Sf9 insect cells.

JAK3

The kinase domain of human JAK3 was amplified from U937mRNA using the polymerase chain reaction with the following primers:

```
                                    (SEQ ID NO: 5)
XHOI-J3   5'-CCG CTC GAG TAT GCC TGC CAA GAC CCC
          ACG-3'
                                    (SEQ ID NO: 6)
J3-KPNI    5'-CGG GGT ACC CTA TGA AAA GGA CAG GGA
          GTG-3'
```

JAK3 PCR products were cloned into the pFastBac HTb expression vector (Gibco) via the Xho I and Kpn I sites. The JAK3 plasmid was then transformed into competent DH10Bac cells (Gibco), and the recombinant baculovirus produced prepared for transfection into Sf9 insect cells.

TYK2

The kinase domain of human TYK2 was amplified from A549 mRNA using the polymerase chain reaction with the following primers:

```
                                    (SEQ ID NO: 7)
HT2EK     5'-GGA GCA CTC GAG ATG GTA GCA CAC AAC
          CAG GTG-3'
                                    (SEQ ID NO: 8)
ITY2.2R   5'-GGA GCA GGA ATT CCG GCG CTG CCG GTC
          AAA TCT GG-3'
```

TYK2 PCR products were cloned into pBlueBacHis2A (Invitrogen) via the EcoRI site. The recombinant TYK2 baculovirus produced was prepared for transfected into Sf9 insect cells.

Large Scale Production Of Kinase Domains

Baculovirus preparations from each of the JAK family members were infected into five liters of High Five cells (Invitrogen) grown in High Five serum free medium (Invitrogen) to a cell density of approximately $1-2 \times 10^6$ cells/ml. Cells are infected with virus at a MOI of 0.8-3.0. Cells were harvested and lysed. JAK kinase domains were purified by affinity chromatography on a Probond (Invitrogen) nickel chelate affinity column.

Assay Protocols

Kinase assays were performed in a 96 well capture-based ELISA assay or in 384 well Optiplates (Packard) using an Alphascreen Protein Tyrosine Kinase kit. In either case using approximately 1.5 µg of affinity purified PTK domain in the presence of 50 mM HEPES, pH 7.5, 10 mM $MgCl_2$, 150 mM NaCl and 10 µM-1 mM ATP. The biotinylated substrate biotin-EGPWLEEEEEAYGWMDF-$NH_2$ (SEQ ID NO:9) (final concentration 5 µM) was used as substrate. In the ELISA assay tyrosine phosphorylation was quantitated following transfer to an avidin coated ELISA plate using peroxidase-linked anti-phosphotyrosine antibody PY20. In the Alphascreen assay, Alphascreen phosphotyrosine acceptor beads followed by streptavidin donor beads were added under subdued light. The ELISA plates were read on a BMG Fluorostar, the Alphascreen plates were read on a Packard Fusion Alpha. Inhibitors were added to the assays fifteen minutes prior to the addition of ATP. Inhibitors were added in aqueous DMSA, with DMSA concentrations never exceeding 1%.

Results

The activity of a range of compounds is shown in Table 2. Compounds that exhibited a capacity to inhibit 50% or greater of enzyme activity at a concentration of 10 μM (measured under standard conditions, see Methods), are designated as "+". Compounds not tested are designated "NT"; while compounds that did not inhibit enzyme activity by 50% at 10 μM are designated "−".

TABLE 2

| CHEMISTRY | Jak2 | Jak3 | abl | fes | fms | hck | Zap70 |
|---|---|---|---|---|---|---|---|
| C23H24N2O6 | NT | NT | − | − | − | − | − |
| C17H20N2O5 | NT | NT | − | − | − | − | + |
| C15H16N2O4 | − | − | − | − | NT | − | − |
| C22H22N2O4 | − | − | + | − | + | + | − |
| C17H19NO4 | − | − | − | − | + | − | − |

TABLE 2-continued

| CHEMISTRY | Jak2 | Jak3 | abl | fes | fms | hck | Zap70 |
|---|---|---|---|---|---|---|---|
| C20H18N2O2 | − | NT | − | − | NT | − | − |
| C19H14Cl2N2O2 | − | − | − | − | NT | − | − |
| C18H14N2O2 | − | − | − | NT | − | − | − |
| C21H20N2O4 | − | − | − | − | − | NT | − |
| C19H15FN2O2 | NT | − | − | − | NT | − | − |

TABLE 2-continued
| CHEMISTRY | Jak2 | Jak3 | abl | fes | fms | hck | Zap70 |
|---|---|---|---|---|---|---|---|
| 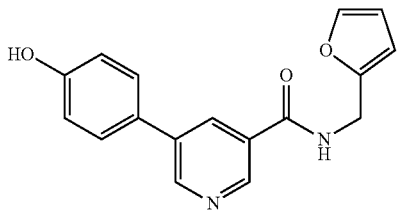<br>C17H14N2O3 | − | − | − | − | + | − | − |
| 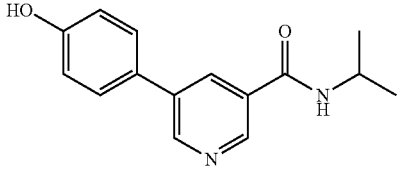<br>C15H16N2O2 | − | NT | − | − | + | − | − |
| 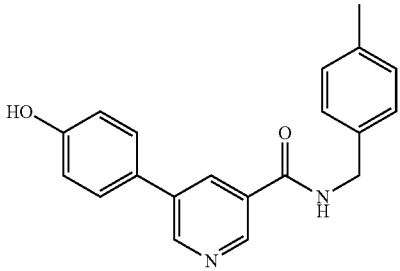<br>C20H18N2O2 | − | − | − | NT | − | − | − |
| 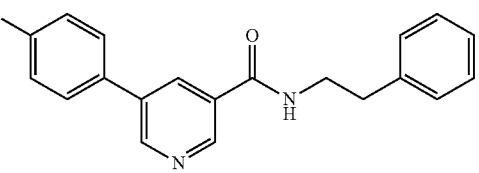<br>C20H18N2O2 | − | − | NT | − | − | − | − |
| 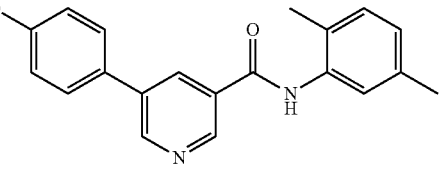<br>C20H18N2O2 | − | − | − | NT | − | + | − |
| 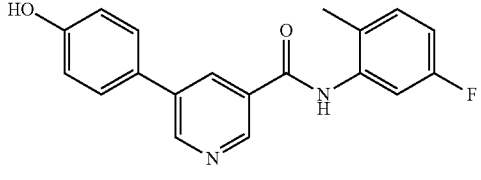<br>C19H15FN2O2 | − | − | + | − | − | NT | − |

TABLE 2-continued
| CHEMISTRY | Jak2 | Jak3 | abl | fes | fms | hck | Zap70 |
|---|---|---|---|---|---|---|---|
| 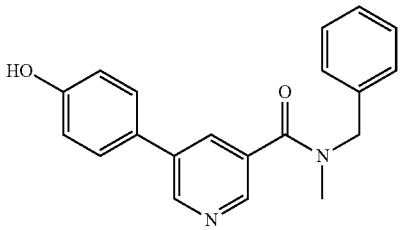 C20H18N2O2 | − | − | NT | − | − | − | − |
| 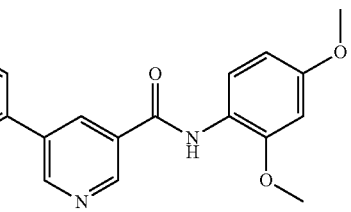 C20H18N2O4 | − | − | − | NT | NT | − | − |
| 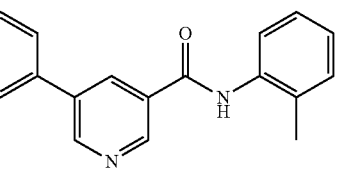 C19H16N2O2 | − | − | NT | − | + | + | − |
| 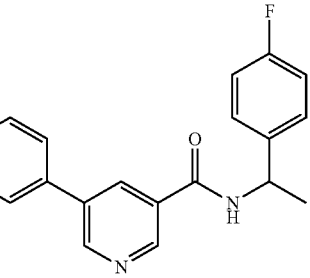 C20H17FN2O2 | − | − | − | − | NT | − | − |
| 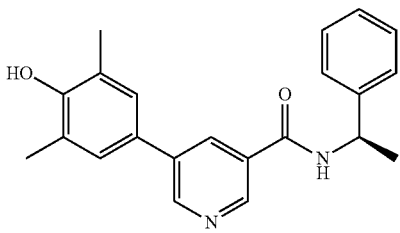 C22H22N2O2 | − | NT | − | − | NT | − | − |

TABLE 2-continued
| CHEMISTRY | Jak2 | Jak3 | abl | fes | fms | hck | Zap70 |
|---|---|---|---|---|---|---|---|
| 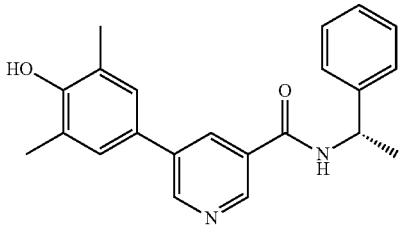<br>C22H22N2O2 | − | NT | − | − | − | NT | − |
| 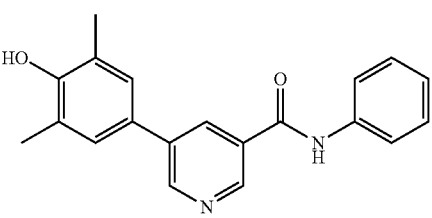<br>C20H18N2O2 | − | − | − | NT | − | + | − |
| 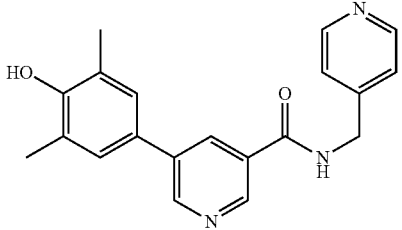<br>C20H19N3O2 | − | − | − | − | + | − | − |
| 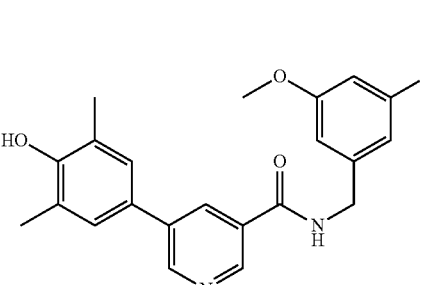<br>C23H24N2O4 | − | − | NT | − | + | − | − |
| 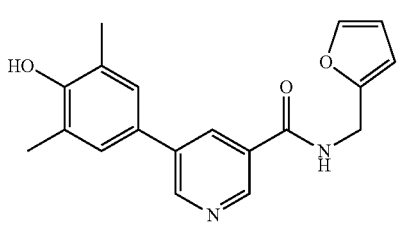<br>C19H18N2O3 | − | − | − | − | − | − | + |

TABLE 2-continued
| CHEMISTRY | Jak2 | Jak3 | abl | fes | fms | hck | Zap70 |
|---|---|---|---|---|---|---|---|
| 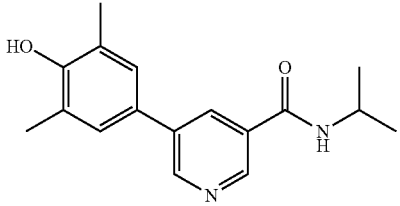<br>C17H20N2O2 | − | − | − | − | − | − | + |
| 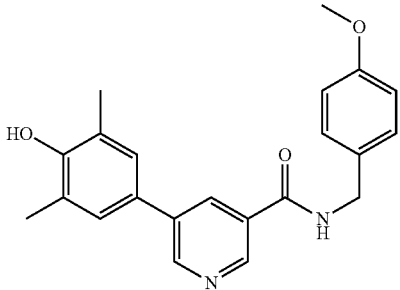<br>C22H22N2O3 | NT | − | − | − | − | − | − |
| 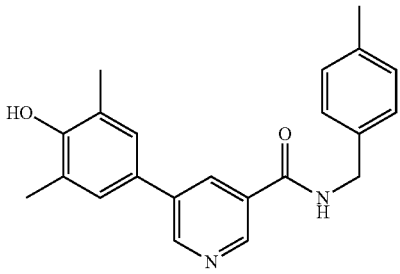<br>C22H22N2O2 | − | − | − | − | NT | − | |
| 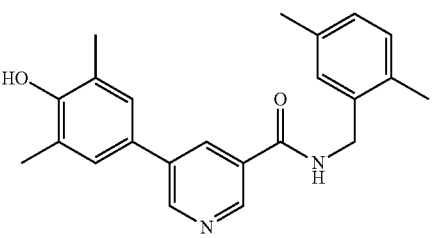<br>C22H22N2O2 | − | − | + | + | + | NT | − |
| 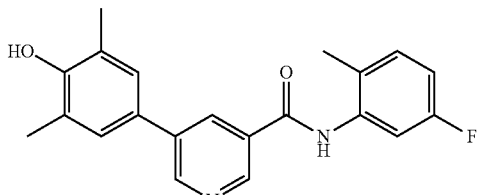<br>C21H19FN2O2 | − | − | NT | NT | + | + | − |

TABLE 2-continued
| CHEMISTRY | Jak2 | Jak3 | abl | fes | fms | hck | Zap70 |
|---|---|---|---|---|---|---|---|
| 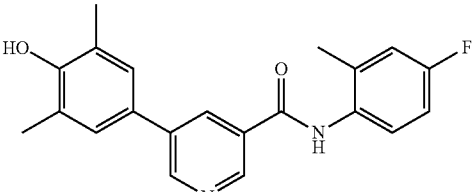 C21H19FN2O2 | − | − | + | − | + | + | NT |
| 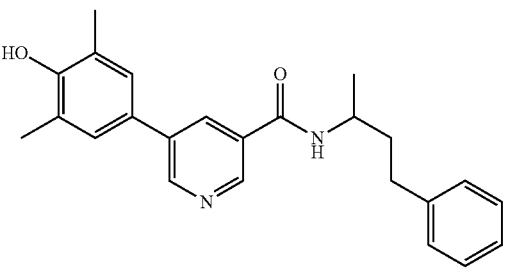 C24H26N2O2 | − | − | NT | − | − | − | − |
| 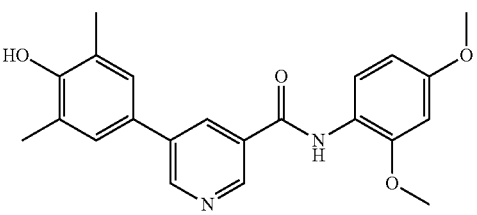 C22H22N2O4 | − | − | − | − | NT | NT | − |
| 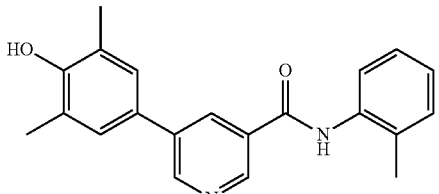 C21H20N2O2 | − | − | + | NT | + | + | − |
| 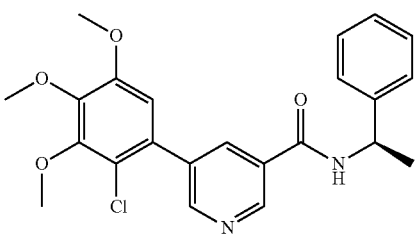 C23H23ClN2O4 | − | − | − | − | − | − | NT |
| 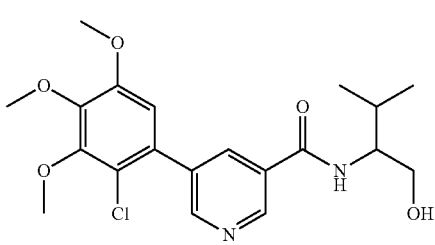 C20H25ClN2O5 | − | − | − | NT | − | NT | − |

TABLE 2-continued
| CHEMISTRY | Jak2 | Jak3 | abl | fes | fms | hck | Zap70 |
|---|---|---|---|---|---|---|---|
| 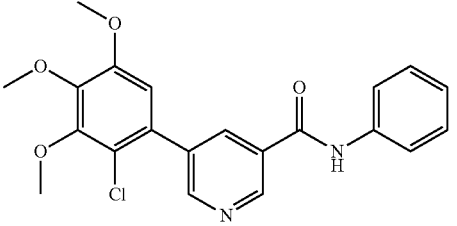<br>C21H19ClN2O4 | – | – | – | – | NT | – | – |
| 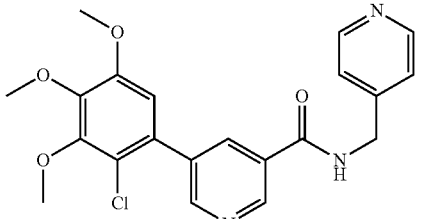<br>C21H20ClN3O4 | – | NT | – | – | – | – | – |
| 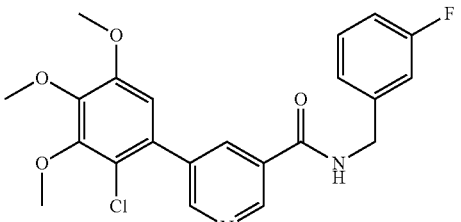<br>C22H20ClFN2O4 | – | – | – | – | – | NT | – |
| 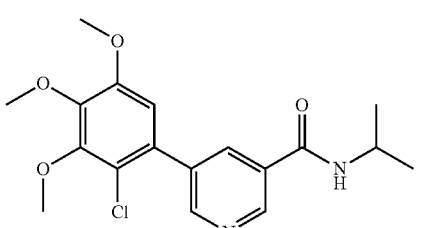<br>C18H21ClN2O4 | – | – | NT | – | – | – | – |
| 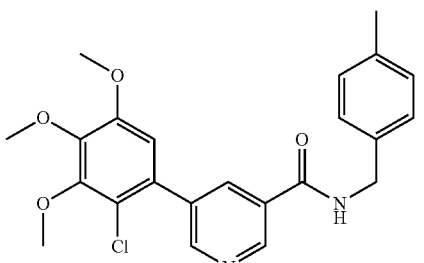<br>C23H23ClN2O4 | – | – | – | – | NT | NT | – |

TABLE 2-continued
| CHEMISTRY | Jak2 | Jak3 | abl | fes | fms | hck | Zap70 |
|---|---|---|---|---|---|---|---|
| 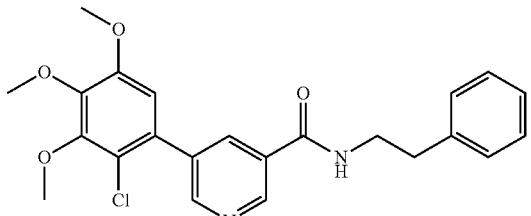<br>C23H23ClN2O4 | − | − | NT | − | − | − | − |
| 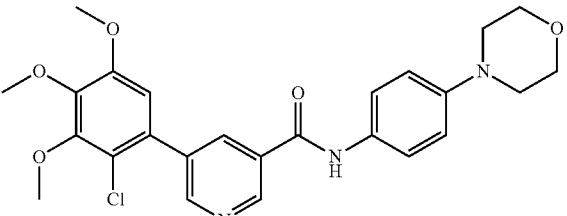<br>C25H26ClN3O5 | − | − | − | − | NT | − | |
| 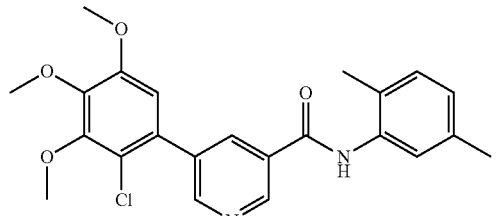<br>C23H23ClN2O4 | − | − | − | − | + | + | NT |
| 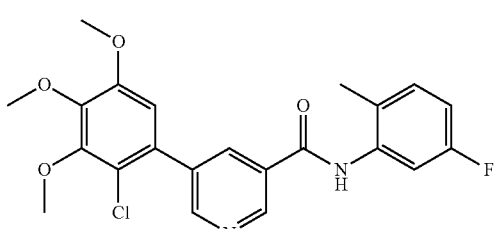<br>C22H20ClFN2O4 | − | − | − | − | + | + | − |
| 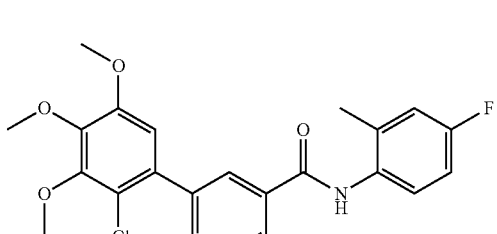<br>C22H20ClFN2O4 | − | − | NT | − | + | + | − |

TABLE 2-continued
| CHEMISTRY | Jak2 | Jak3 | abl | fes | fms | hck | Zap70 |
|---|---|---|---|---|---|---|---|
| 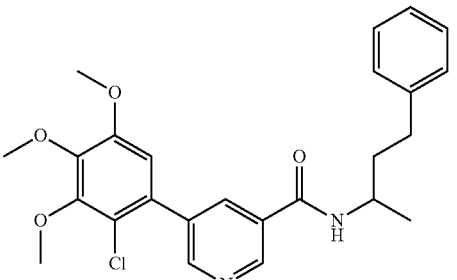 C25H27ClN2O4 | − | − | − | NT | − | − | − |
| 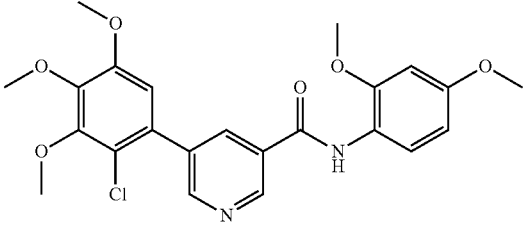 C23H23ClN2O6 | − | − | − | − | NT | − | − |
| 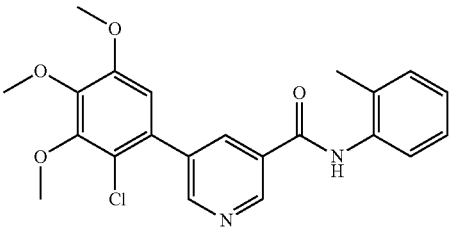 C22H21ClN2O4 | − | − | − | − | + | + | − |
| 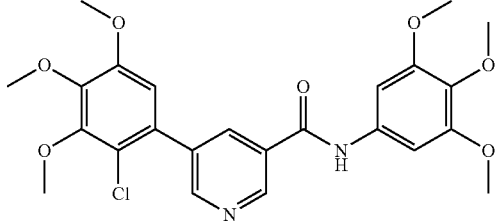 C24H25ClN2O7 | − | − | NT | − | − | − | − |
| 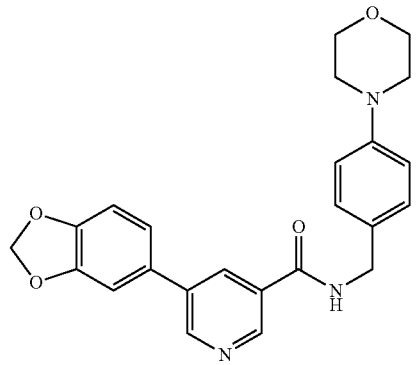 C24H23N3O4 | − | − | − | − | − | − | NT |

TABLE 2-continued
| CHEMISTRY | Jak2 | Jak3 | abl | fes | fms | hck | Zap70 |
|---|---|---|---|---|---|---|---|
| 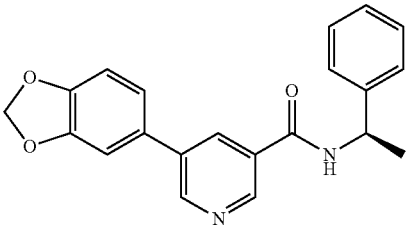<br>C21H18N2O3 | - | - | NT | - | - | - | - |
| 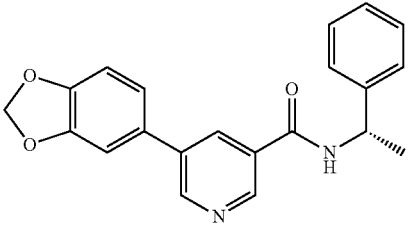<br>C21H18N2O3 | - | - | NT | - | - | - | - |
| 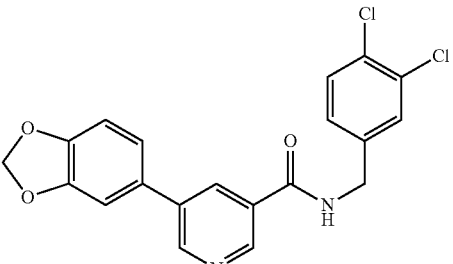<br>C20H14Cl2N2O3 | - | - | NT | - | - | NT | - |
| 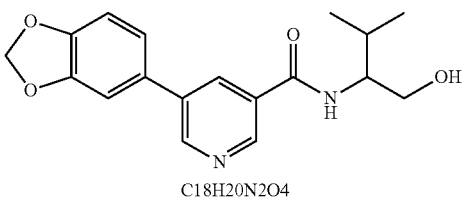<br>C18H20N2O4 | NT | - | - | - | - | - | - |
| 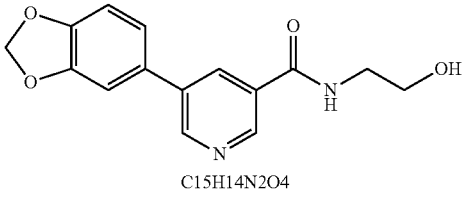<br>C15H14N2O4 | - | - | - | NT | NT | - | - |
| 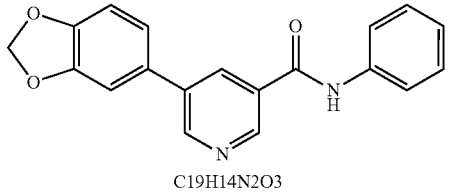<br>C19H14N2O3 | - | - | - | - | - | NT | - |

TABLE 2-continued
| CHEMISTRY | Jak2 | Jak3 | abl | fes | fms | hck | Zap70 |
|---|---|---|---|---|---|---|---|
| 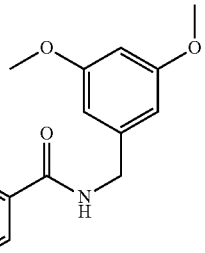<br>C22H20N2O5 | − | NT | − | − | NT | − | − |
| 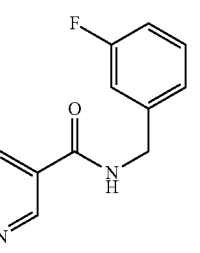<br>C20H16FN2O3 | − | − | − | − | NT | − | − |
| 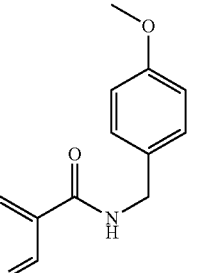<br>C21H18N2O4 | − | − | NT | − | − | − | − |
| 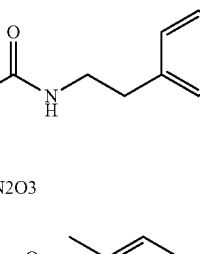<br>C21H18N2O3 | − | − | − | NT | − | − | − |
| 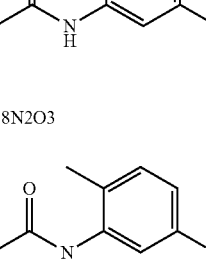<br>C21H18N2O3 | − | − | − | − | − | NT | − |
| 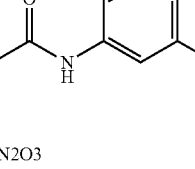<br>C20H15FN2O3 | − | − | − | − | − | − | − |

TABLE 2-continued
| CHEMISTRY | Jak2 | Jak3 | abl | fes | fms | hck | Zap70 |
|---|---|---|---|---|---|---|---|
| 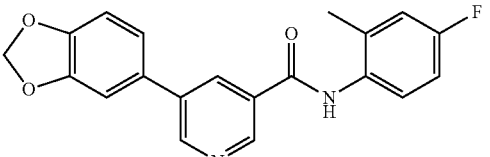 C20H15FN2O3 | – | – | – | NT | – | – | – |
| 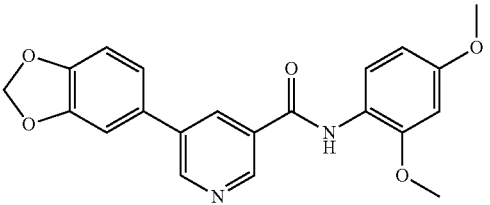 C21H18N2O5 | – | – | NT | – | – | – | NT |
| 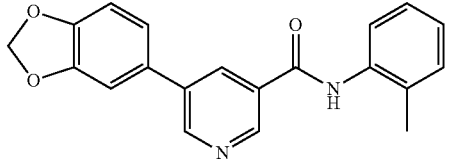 C20H16N2O3 | – | – | – | – | NT | + | – |
| 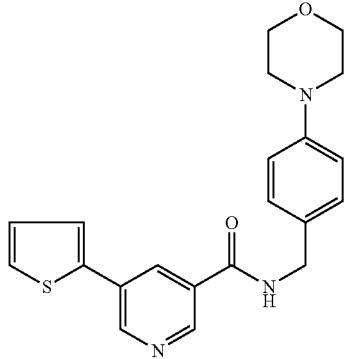 C21H21N3O2S | – | NT | – | – | NT | – | – |
| 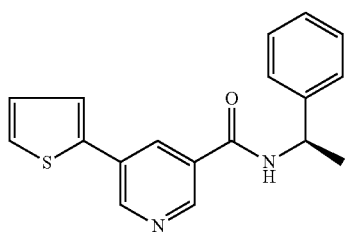 C18H16N2OS | – | – | – | – | NT | – | – |

TABLE 2-continued
| CHEMISTRY | Jak2 | Jak3 | abl | fes | fms | hck | Zap70 |
|---|---|---|---|---|---|---|---|
| 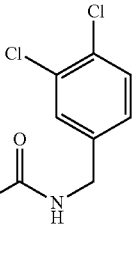<br>C17H12Cl2N2OS | − | − | NT | − | − | − | − |
| 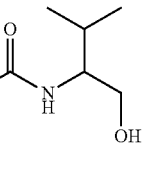<br>C15H18N2O2S | − | − | NT | − | − | − | − |
| 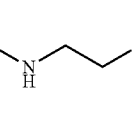<br>C12H12N2O2S | − | − | − | − | NT | − | |
| 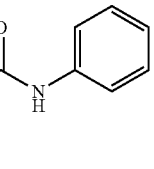<br>C16H12N2OS | − | − | − | + | − | − | − |
| 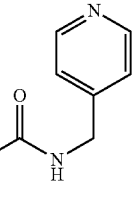<br>C16H13N3OS | − | − | NT | − | − | − | − |
| 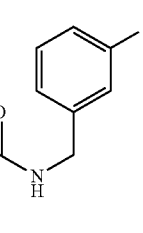<br>C17H13FN2OS | − | − | − | + | − | − | NT |

TABLE 2-continued
| CHEMISTRY | Jak2 | Jak3 | abl | fes | fms | hck | Zap70 |
|---|---|---|---|---|---|---|---|
| 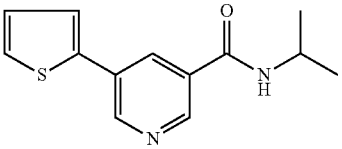 C13H14N2OS | − | − | − | + | + | − | − |
| 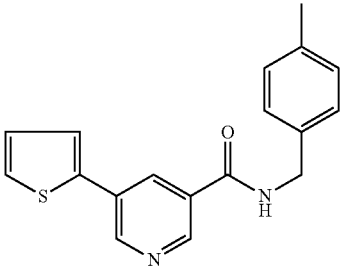 C18H16N2OS | NT | − | − | + | − | − | − |
| 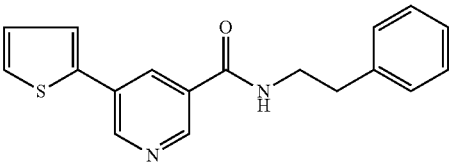 C18H16N2OS | − | − | − | − | NT | − | − |
| 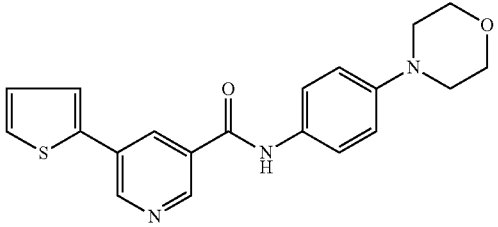 C20H19N3O2S | − | − | − | + | − | − | − |
| 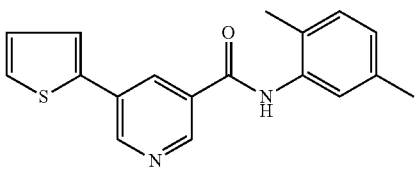 C18H16N2OS | − | − | − | + | − | NT | − |
| 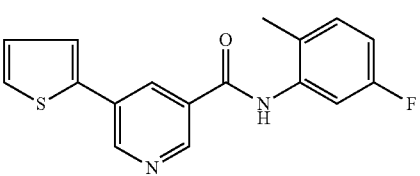 C17H13FN2OS | − | − | − | − | + | + | − |

TABLE 2-continued
| CHEMISTRY | Jak2 | Jak3 | abl | fes | fms | hck | Zap70 |
|---|---|---|---|---|---|---|---|
| 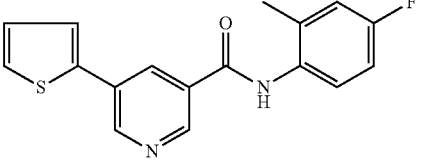 C17H13FN2OS | NT | − | − | − | − | NT | − |
| 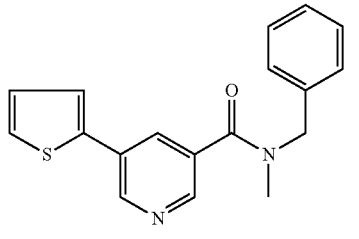 C18H16N2OS | − | − | − | + | − | − | − |
| 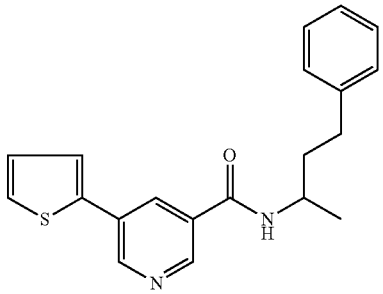 C20H20N2OS | − | − | − | + | − | − | − |
| 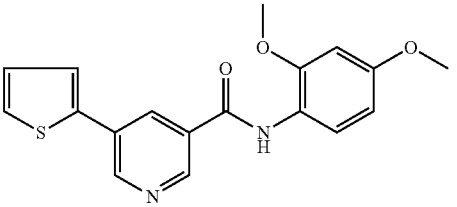 C18H16N2O3S | − | NT | − | − | − | − | − |
| 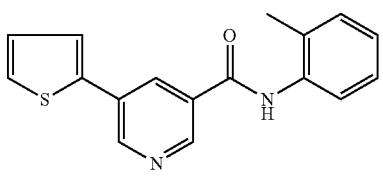 C17H14N2OS | − | − | − | − | NT | + | − |
| 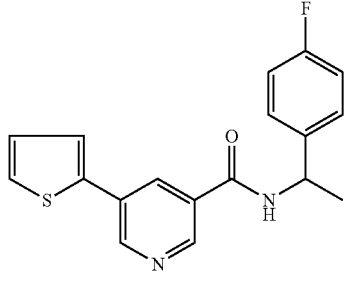 C18H15FN2OS | − | − | − | + | − | − | − |

TABLE 2-continued
| CHEMISTRY | Jak2 | Jak3 | abl | fes | fms | hck | Zap70 |
|---|---|---|---|---|---|---|---|
| 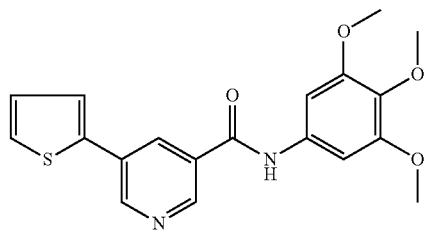 C19H18N2O4S | − | NT | − | − | − | − | − |
| 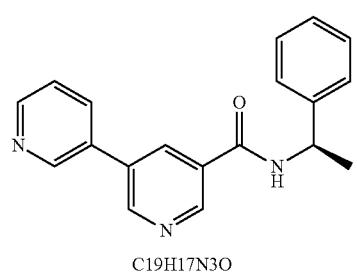 C19H17N3O | − | − | − | − | − | − | NT |
|  C16H19N3O2 | NT | − | − | − | − | − | − |
| 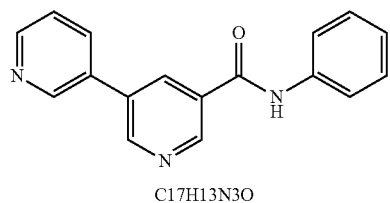 C17H13N3O | − | − | − | − | − | − | + |
| 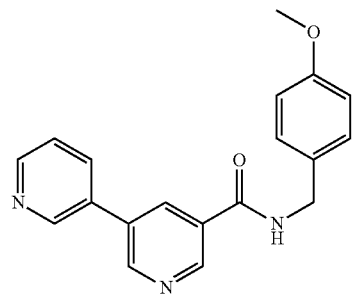 C19H17N3O2 | − | − | − | NT | − | − |
| 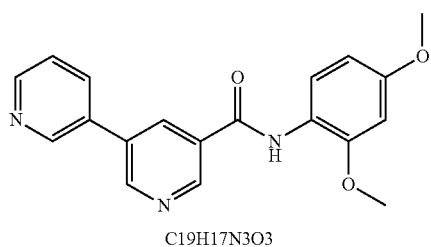 C19H17N3O3 | + | + | − | − | + | − | − |

TABLE 2-continued
| CHEMISTRY | Jak2 | Jak3 | abl | fes | fms | hck | Zap70 |
|---|---|---|---|---|---|---|---|
| 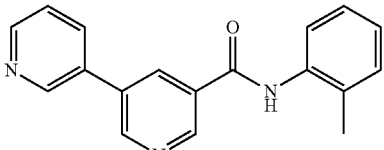<br>C18H15N3O | – | – | – | – | – | NT | – |
| 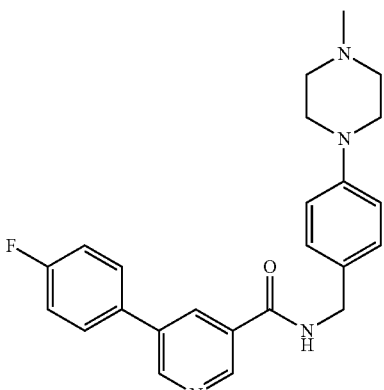<br>C24H25FN4O | – | – | NT | – | – | NT | – |
| 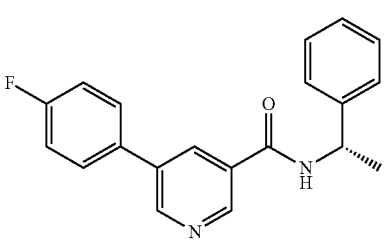<br>C20H17FN2O | – | – | – | NT | – | – | – |
| 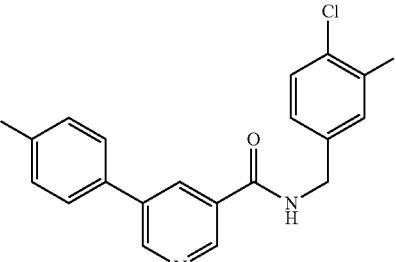<br>C19H13Cl2FN2O | – | – | – | – | – | – | NT |
| 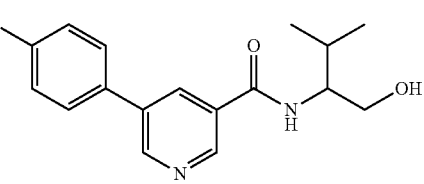<br>C17H19FN2O2 | – | NT | – | – | – | – | – |

TABLE 2-continued
| CHEMISTRY | Jak2 | Jak3 | abl | fes | fms | hck | Zap70 |
|---|---|---|---|---|---|---|---|
| 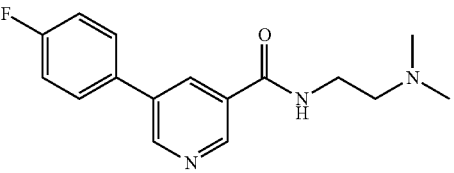<br>C16H18FN3O | − | − | − | − | − | − | − |
| 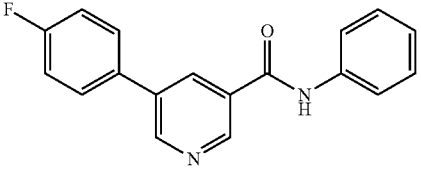<br>C18H13FN2O | − | − | − | − | − | − | NT |
| 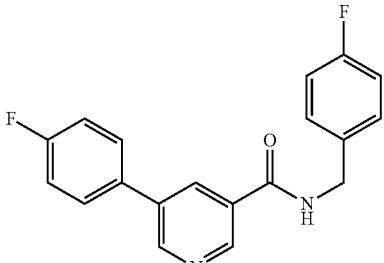<br>C19H14F2N2O | + | − | − | − | − | NT | − |
| 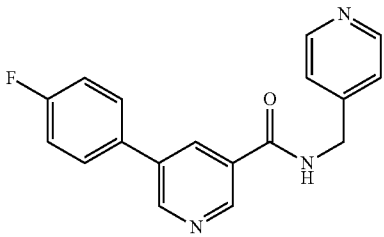<br>C18H14FN3O | − | − | − | − | − | NT | − |
| 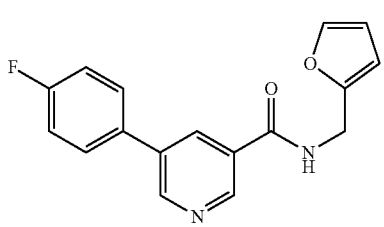<br>C17H13FN2O2 | − | + | − | NT | − | − | − |
| 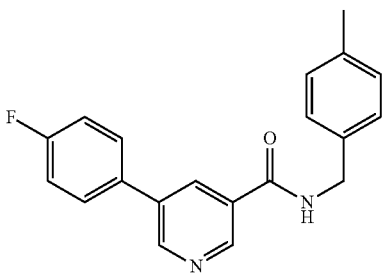<br>C20H17FN2O | − | NT | − | − | − | − | − |

TABLE 2-continued

| CHEMISTRY | Jak2 | Jak3 | abl | fes | fms | hck | Zap70 |
|---|---|---|---|---|---|---|---|
| C23H23FN4O | − | − | − | NT | − | NT | − |
| C21H19FN2O2 | − | − | − | − | − | − | + |
| C20H17FN2O | − | − | NT | − | − | − | − |
| C19H14F2N2O | − | − | − | − | NT | − | − |
| C20H17FN2O | − | NT | − | − | − | − | − |
| C18H17FN4O | − | − | NT | − | − | NT | − |

TABLE 2-continued
| CHEMISTRY | Jak2 | Jak3 | abl | fes | fms | hck | Zap70 |
|---|---|---|---|---|---|---|---|
| 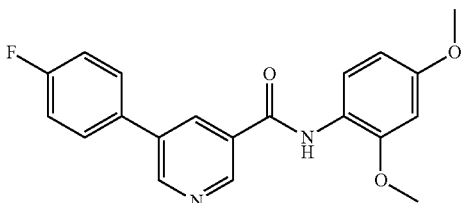<br>C20H17FN2O3 | – | – | – | – | – | NT | – |
| 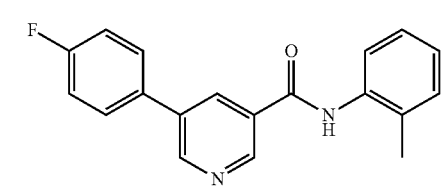<br>C19H15FN2O | – | – | – | – | NT | NT | – |
| 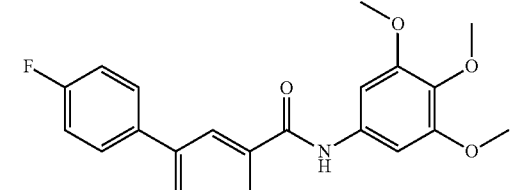<br>C21H19FN2O4 | – | – | – | NT | – | – | – |
| 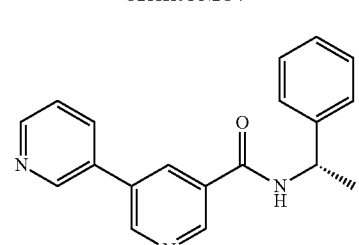<br>C19H17N3O | – | – | NT | – | – | NT | – |
| 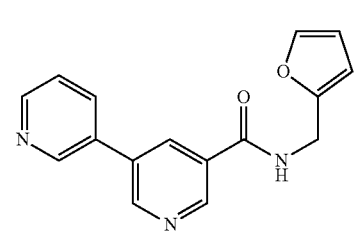<br>C16H13N3O2 | – | – | NT | – | – | NT | – |
| 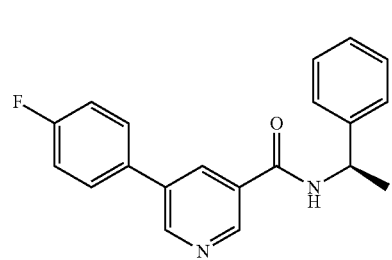<br>C20H17FN2O | – | – | NT | – | – | NT | – |

TABLE 2-continued

| CHEMISTRY | Jak2 | Jak3 | abl | fes | fms | hck | Zap70 |
|---|---|---|---|---|---|---|---|
| C24H25ClN2O6 | + | − | − | − | − | − | + |
| C21H20N2O2 | − | − | − | − | NT | − | − |
| C21H20N2O2 | − | − | − | − | NT | − | − |
| C19H17N3O2 | − | − | NT | − | − | − | + |
| C19H16N2O2 | − | − | − | − | − | − | NT |

TABLE 2-continued

| CHEMISTRY | Jak2 | Jak3 | abl | fes | fms | hck | Zap70 |
|---|---|---|---|---|---|---|---|
| C22H22N2O4 | − | − | − | − | − | − | + |
| C18H16N2O3 | − | − | − | − | − | − | + |
| C21H20N2O3 | − | − | − | − | − | − | + |
| C21H20N2O2 | − | − | − | − | − | − | + |
| C21H20N2O2 | − | − | − | − | − | − | + |

TABLE 2-continued

| CHEMISTRY | Jak2 | Jak3 | abl | fes | fms | hck | Zap70 |
|---|---|---|---|---|---|---|---|
| C22H22N2O3 | − | − | − | − | − | − | + |
| C21H20N2O2 | − | − | − | − | − | + | + |
| C20H17FN2O2 | − | − | − | − | NT | NT | + |
| C20H17FN2O2 | − | − | − | − | − | + | NT |
| C23H24N2O2 | − | NT | − | − | − | − | − |

TABLE 2-continued
| CHEMISTRY | Jak2 | Jak3 | abl | fes | fms | hck | Zap70 |
|---|---|---|---|---|---|---|---|
| 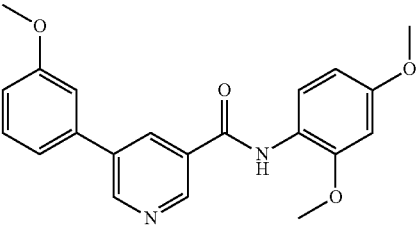<br>C21H20N2O4 | − | − | − | − | − | − | NT |
| 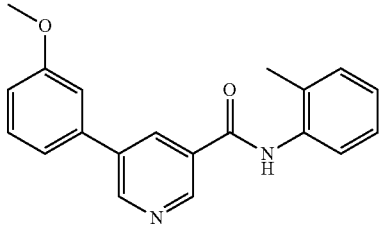<br>C20H18N2O2 | − | − | − | − | − | NT | − |
| 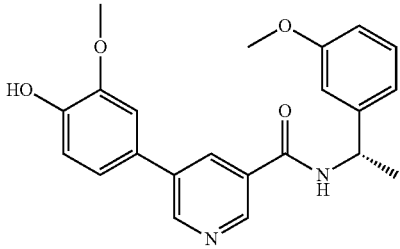<br>C22H22N2O4 | − | − | NT | − | − | − | − |
| 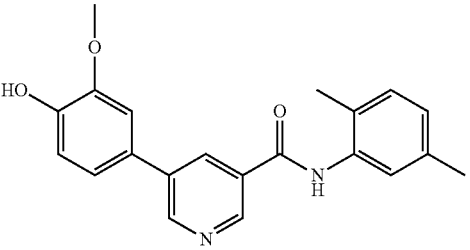<br>C21H20N2O3 | − | − | + | NT | + | + | − |
| 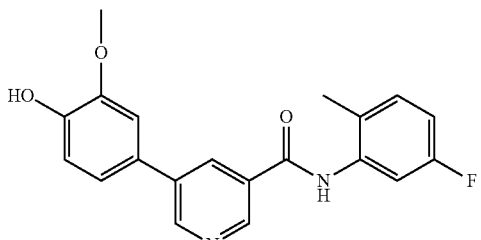<br>C20H17FN2O3 | − | − | + | − | + | + | NT |

TABLE 2-continued

| CHEMISTRY | Jak2 | Jak3 | abl | fes | fms | hck | Zap70 |
|---|---|---|---|---|---|---|---|
| C20H17FN2O3 | − | − | + | − | − | + | − |
| C20H18N2O3 | − | − | NT | − | − | + | − |
| C19H16FN3O | NT | − | − | − | − | − | − |
| C19H17N3O | − | − | − | NT | − | − | + |
| C18H14FN3O | NT | NT | − | + | − | − | − |
| C18H14FN3O | NT | NT | − | − | − | − | − |

TABLE 2-continued

| CHEMISTRY | Jak2 | Jak3 | abl | fes | fms | hck | Zap70 |
|---|---|---|---|---|---|---|---|
| 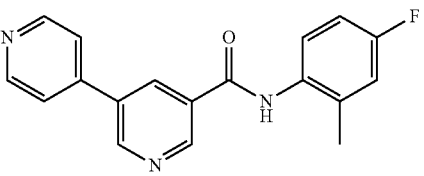 C18H14FN3O | NT | NT | – | – | – | – | – |
| 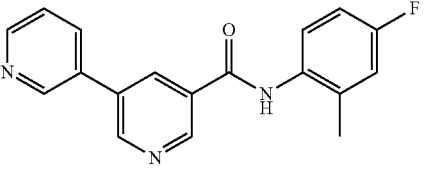 C18H14FN3O | NT | NT | – | – | – | – | – |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of formula I

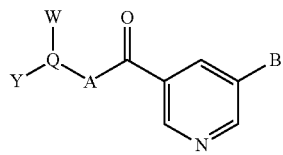

or a pharmaceutically acceptable salt or diastereomer thereof, wherein:

A is $NR^1$, where $R^1$ is H or $C_{1-4}$ alkyl;

B is phenyl optionally substituted with 0-4 substituents independently selected from halogen, $C_{1-4}$ alkyl, $CF_3$, CN, aryl, OH, $OCF_3$, $OC_{1-4}$ alkyl, $OC_{2-5}$ alkyl$NR^2R^3$, Oaryl, $CO_2R^2$, $CONR^2R^3$, $NR^2R^3$, $NR^4C_{1-4}$ alkyl$NR^2R^3$, $NR^2COR^3$, $OC(O)NR^2R^3$, $NR^4CONR^2R^3$, and $NR^2SO_2R^3$;

wherein $R^2$ and $R^3$ are each independently H, $C_{1-4}$ alkyl, aryl, or $C_{1-4}$ alkyl aryl;

wherein $R^4$ is H or $C_{1-4}$ alkyl; and wherein $R^5$ is H or $C_{1-4}$ alkyl;

Q is a bond when W is absent, and is $C_{1-4}$ alkyl when W is present;

W is selected from H, $C_{1-4}$ alkyl, and $C_{2-6}$ alkenyl; where $C_{1-4}$ alkyl or $C_{2-6}$ alkenyl may be optionally substituted with $C_{1-4}$ alkyl, OH, $OC_{1-4}$ alkyl, $NR^6C(O)R^7$, $CONR^6R^7$, $OR^6$, or $NR^6R^7$;

wherein $R^6$ and $R^7$ are each independently H, $C_{1-4}$alkyl, $C_{1-4}$ alkyl cycloalkyl, or aryl, and Y is phenyl, optionally substituted with 0-3 substituents independently selected from halogen, $C_{1-4}$ alkyl, $CF_3$, aryl, OH, $OCF_3$, $C_{2-4}$ alkynyl, $OC_{1-4}$ alkyl, $OC_{2-5}$ alkyl$NR^9R^{10}$, Oaryl, $CONR^9R^{10}$, $C_{1-4}$alkyl$NR^9R^{10}$, $NR^{11}C_{1-4}$ alkyl$NR^9R^{10}$, $NR^9COR^{10}$, $NR^{11}CONR^9R^{10}$, and $NR^9SO_2R^{10}$;

wherein $R^9$ and $R^{10}$ are each independently H, $C_{1-4}$ alkyl, aryl, or $C_{1-4}$ alkyl aryl; and wherein $R^{11}$ is H or $C_{1-4}$ alkyl.

2. A compound according to claim 1 or a pharmaceutically acceptable salt or diastereomer thereof, wherein:

W is selected from H, $C_{1-4}$ alkyl, and $C_{2-6}$ alkenyl; wherein $C_{1-4}$ alkyl or $C_{2-6}$ alkenyl may be optionally substituted with $C_{1-4}$ alkyl, OH, $OC_{1-4}$ alkyl, or $NR^6R^7$;

wherein $R^6$ and $R^7$ are each independently H, $C_{1-4}$ alkyl, $C_{1-4}$ alkyl cycloalkyl, aryl;

Y is phenyl optionally substituted with 0-3 substituents independently selected from halogen, $C_{1-4}$ alkyl, $CF_3$, aryl, OH, $OCF_3$, $OC_{1-4}$ alkyl, $OC_{2-5}$ alkyl$NR^9R^{10}$, Oaryl, $CONR^9R^{10}$, $C_{1-4}$ alkyl$NR^9R^{10}$, $NR^{11}C_{1-4}$ alkyl$NR^9R^{10}$, $NR^9COR^{10}$, $NR^{11}CONR^9R^{10}$, and $NR^9SO_2R^{10}$;

wherein $R^9$ and $R^{10}$ are each independently H, $C_{1-4}$ alkyl, aryl, or $C_{1-4}$ alkyl aryl; and wherein $R^{11}$ is H or $C_{1-4}$ alkyl.

3. A compound selected from the group consisting of:

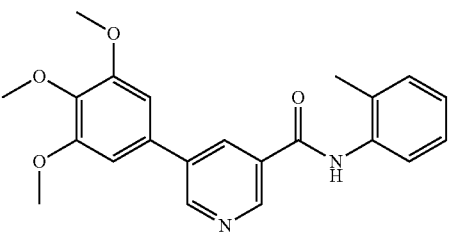

C22H22N2O4

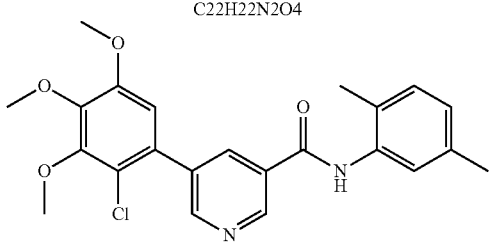

C23H23ClN2O4

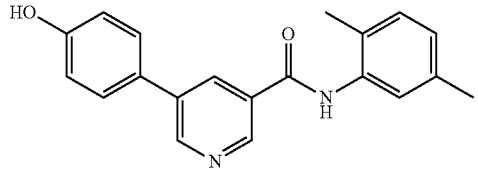

C20H18N2O2

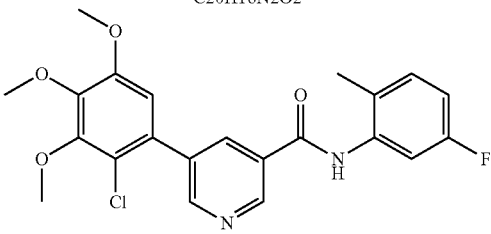

C22H20ClFN2O4

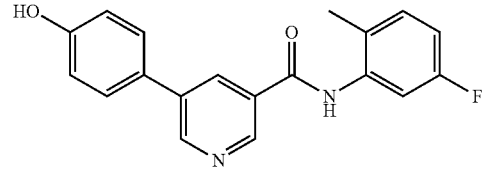

C19H15FN2O2

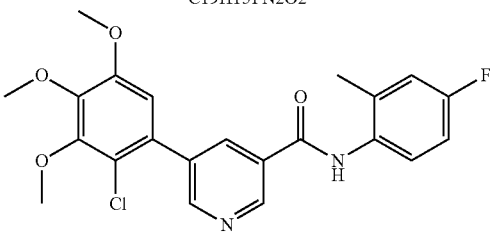

C22H20ClFN2O4

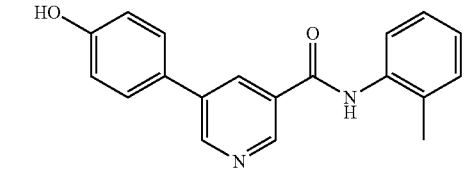

C19H16N2O2

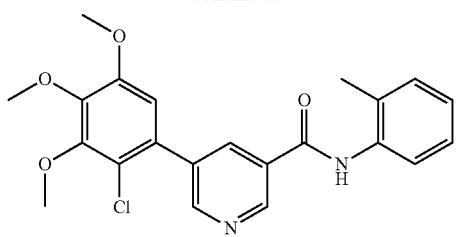
C22H21ClN2O4
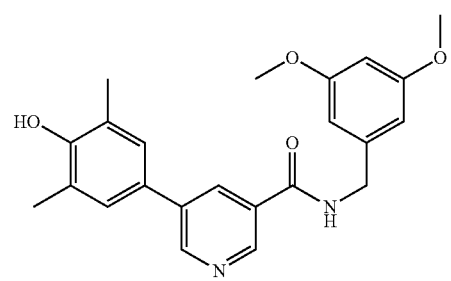
C22H21ClN2O4
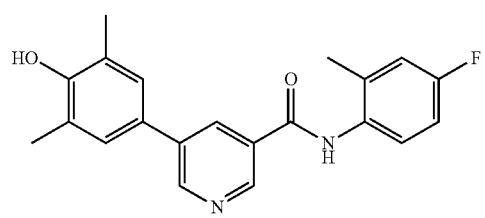
C21H19FN2O2
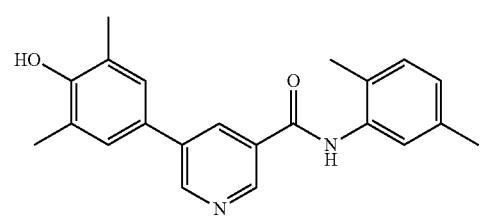
C22H22N2O2
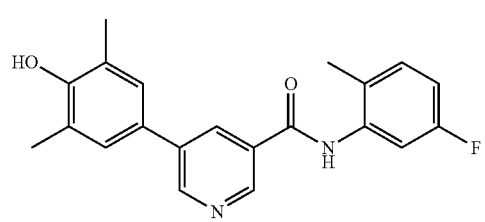
C21H19N2O2
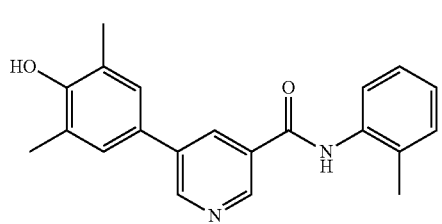
C21H20N2O2
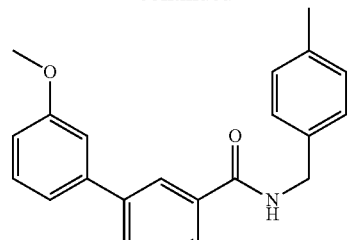
C21H20N2O2
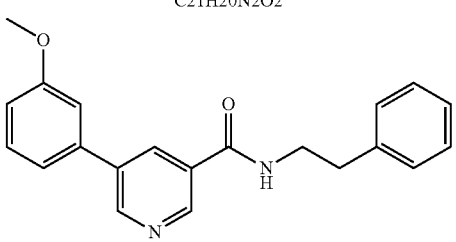
C21H20N2O2
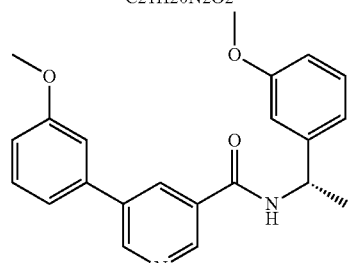
C22H22N2O3
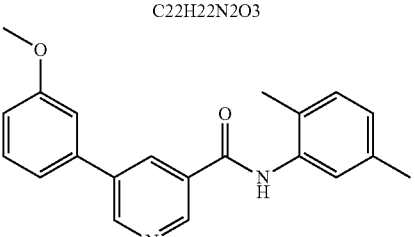
C21H20N2O2
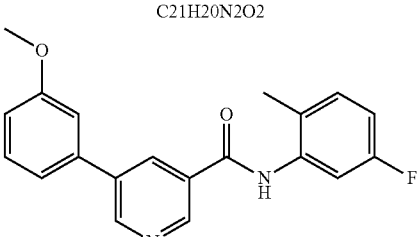
C20H17FN2O2
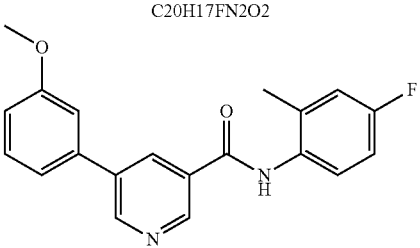
C20H17FN2O2

-continued
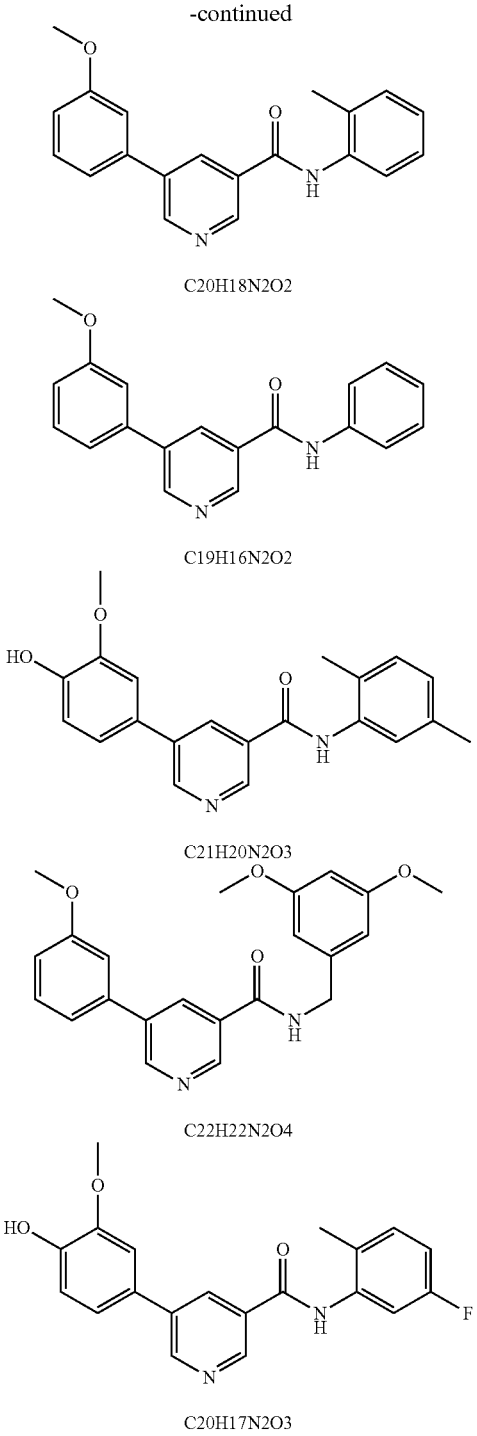
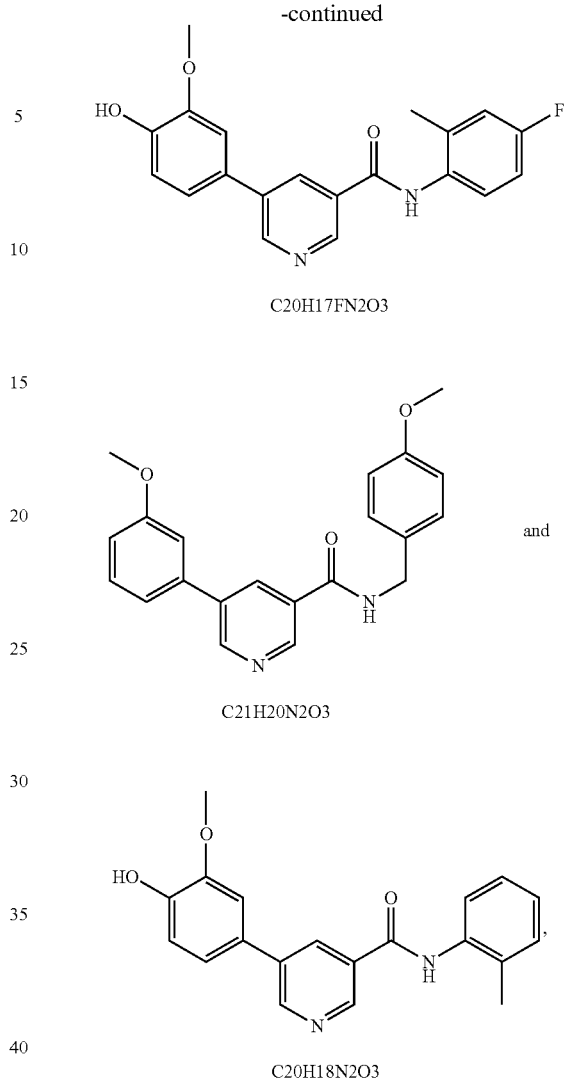
and pharmaceutically acceptable salts or diastereomers thereof.
4. A pharmaceutical composition comprising a carrier and at least one compound of claim 1.
5. A pharmaceutical composition comprising a carrier and at least one compound of claim 2.
6. A pharmaceutical composition comprising a carrier and at least one compound of claim 3.
* * * * *